(12) United States Patent
Wang et al.

(10) Patent No.: US 9,726,114 B2
(45) Date of Patent: Aug. 8, 2017

(54) ACOUSTICALLY TRIGGERED NANO/MICRO-SCALE PROPULSION DEVICES

(71) Applicant: The Regents of the University of California, Oakland, CA (US)

(72) Inventors: Joseph Wang, San Diego, CA (US); Sadik C. Esener, Solana Beach, CA (US); Daniel Kagan, Westfield, NJ (US); Michael Benchimol, San Diego, CA (US); Jonathan Claussen, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 233 days.

(21) Appl. No.: 14/379,279

(22) PCT Filed: Feb. 19, 2013

(86) PCT No.: PCT/US2013/026757
§ 371 (c)(1),
(2) Date: Aug. 15, 2014

(87) PCT Pub. No.: WO2013/123524
PCT Pub. Date: Aug. 22, 2013

(65) Prior Publication Data
US 2015/0013304 A1    Jan. 15, 2015

Related U.S. Application Data

(60) Provisional application No. 61/599,825, filed on Feb. 16, 2012.

(51) Int. Cl.
*F02K 7/00* (2006.01)
*F03G 7/00* (2006.01)
(Continued)

(52) U.S. Cl.
CPC ......... *F02K 7/02* (2013.01); *A61M 37/0092* (2013.01); *B82B 1/006* (2013.01); *B82Y 5/00* (2013.01); *B82Y 30/00* (2013.01); *F03G 7/005* (2013.01)

(58) Field of Classification Search
CPC ...... A61M 37/0092; F02K 7/02; B82Y 30/00; B82Y 5/00
See application file for complete search history.

(56) References Cited

FOREIGN PATENT DOCUMENTS

WO         03099112         12/2003

OTHER PUBLICATIONS

Fuel for Thought Chemically Powered Nanomotors Out Swim Natures Flagellate Bacteria conical multilayer microtubes, Mirkovic, 2010.*

(Continued)

*Primary Examiner* — Gerald L Sung
*Assistant Examiner* — William Breazeal
(74) *Attorney, Agent, or Firm* — Perkins Coie LLP

(57) ABSTRACT

Techniques, devices and systems are disclosed for implementing acoustically triggered propulsion of nano- and micro-scale structures. In one aspect, an ultrasound responsive propulsion device includes a tube that includes one or more layers including an inner layer having an electrostatic surface, and an ultrasound-responsive substance coupled to the inner layer and configured to form gaseous bubbles in a fluid in response to an ultrasound pulse, in which the bubbles exit the tube to propel the tube to move in the fluid.

43 Claims, 13 Drawing Sheets

(51) Int. Cl.
  *B82B 1/00* (2006.01)
  *A61M 37/00* (2006.01)
  *B82Y 30/00* (2011.01)
  *B82Y 5/00* (2011.01)
  *F02K 7/02* (2006.01)

(56) References Cited

OTHER PUBLICATIONS

Alexandroff, A. et al., "BCG immunotherapy of bladder cancer: 20 years", Lancet, 1999 353:1689-1694.
Brujan, E. et al., "Jet formation and shock wave emission during collapse of ultrasound-induced cavitation bubbles and their role in the therapeutic applications of high-intensity focused ultrasound", Phys. Med. Biol., 2005, 50(20), 1797-4809.
Burdick, J. et al., "Synthetic Nanomotors in Microchannel Netowrks: Directional Microchip Motion and Controlled Manipulatin of Cargo", J. Am. Chem. Soc., 2008, 130, 8164-8165.
Calvo-Marzal, P. et al., "Propulsion of nanowire diodes", J. Chem. Comm., 2010, 46, 1623-1627.
Campuzano, S. et al., Bacterial Isolation by Lectin-Modified Microengines, Nanoletters. 2012, 12, 396-401.
Collis, J. et al., "Cavitation microstreaming and stress fields created by microbubbles", Ultrasonics, 2009, 50, 273-279.
Ferrara, K. et al, "Ultrasound Microbubble Contrast Agents: Fundamentals and Application to Gene and Drug Delivery", Ann. Rev. Biomed. Eng., 2007, 9, 415-447.
Gao, W. et al., "Highly Efficient Catalytic Microengines: Template Electrosynthesis of Polyaniline/Platinum Microtubes", Am. Chem. Soc., 2011, 133, 11862-11864.
Gao,W. et al., "Magnetically Powered Flexible Metal Nanowire Motors", J. Am. Chem. Soc., 2010 132, 14403-14405.
Ghosh, A. et al., "Controlled Propulsion of Artificial Magnetic Nanostructured Propellers", Nano Letters, 2009, 6, 2243-2245.
Kagan, D. et al., "Rapid Delivery of Drug Carriers Propelled and Navigated by Catalytic Nanoshuttles", J. Small 2010, 6, 2741-2747.
Kagan, D. et al., "Functionalized Micromachines for Selective and Rapid Isolation of Nucleic Acid Targets from Complex Samples", Nano Letters 2011, 11, 2083-2087.
Mezyk S.P., "Rate Constant Determination for the Reaction of Sulfhydryl Species with the Hydrated Electron in Aqueous Solution", J Phys Chem, 1995, 99, 13970-13975.
Mitragotri, S., "Healing sound: the use of ultrasound in drug delivery and other therapeutic applications", Nat. Rev. Drug Discovery, 2005, 4, 255-260.
Nightingale, K et al., "Acoustic Radiation Force Impulse Imaging: in Vivo Demonstration of Clinical Feasibility", Ultrasound in Medicine & Biology, 2002, 28(2), 227-235.
Orozco, J. et al., "Dynamic Isolation and Unloading of Target Proteins by Aptamer-Modified Microtransporters", J. Anal. Chem. Soc., 2011, 83, 7962-7969.
Sanchez, S. et al., "Microbots Swimming in the Flowing Streams of Microfluidic Channels", J. Anal. Chem. Soc., 2011, 133, 701-703.
Wirde, M. et al., "Self-Assembled Monolayers of Cystamine and Cysteamine on Gold Studied by XPS and Voltammetry", 1999, 15, 6370-6378.
Wong, Z. et al., "Bubble evolution in acoustic droplet vaporization at physiological temperature via ultra-high speed Imaging", Soft Matter 2011, 7, 4009-4016.
Wu, J. et al., "Motion-based DNA detection using catalytic nanomotors", J. Nat. Commun. 1:36 doi: 10.1038/ncomms1035, 2010, 6 pages.
Zhang, L. et al., "Characterizing the Swimming Properties of Artificial Bacterial Flagella", J. Nano Letters 2009, 10, 3663-3667.
Hong, Sung Ran, Authorized Officer, Korean Intellectual Property Office, International Search Report, International Application No. PCT/US2013/026757, Jul. 25, 2013, 12 pages.
Ibsen, S. et al., J. Control Release, Nov. 7, 2011, vol. 155, No. 3, pp. 358-366.
Klibanov, A.L. et al., J Control Release, 20 Nov. 20, vol. 148, No. 1, pp. 13-17.
Huang, S. L. et al., Biochimica et Biophysica Acta., Aug. 12, 2004, vol. 1665, pp. 134-141.
Kagan, D. et al., Angew, Chem. Jun. 12, 2012, vol. 124, pp. 7637-7640.
Wang, W. et al., "Autonomous Motion of Metallic Microrods Propelled by Ultrasound", ACS Nano, vol. 6, No. 7, 2012, pp. 6122-6132.
Mei, Yongfeng et al., "Rolled-up nanotech on polymers: from basic perception to self-propelled catalytic microengines," Chemical Society Reviews, vol. 40, No. 5, May 2011, pp. 2109-2119.
Mirkovic, Tihana et al., "Nanolocomotion—Catalytic Nanomotors and Nanorotors," small, 2010, 6, No. 2, pp. 159-167.
Solovev, Alexander a. et al., "Catalytic Microtubular Jet Engines Self-Propelled by Accumulated Gas Bubbles**", small, 2009, 5, No. 14, pp. 1688-1692.
Fischer, Thorsten et al., "A smart dust biosensor powered by kinesin motors," Nature Nanotechnology, vol. 4, Mar. 2009, pp. 162-166.
Sanchez, Samuel et al., "Microbots Swimming in the Flowing Streams of Microfluidic Channels", American Journal of the Chemical Society, 2011, 133, pp. 701-703.
Fan, Donglei et al., "Sub-Cellular Resolution Delivery of a Cytokine via Precisely Manipulated Nanowires", Nature Nanotechnology, 2010, pp. 545-55.
Howse, Jonathan R. et al., "Self-Motile Colloidal Particles: From Directed Propulsion to Random Walk", Physical Review Letters, 99, 048102 (2007), 4 pages.
Park, Hong-Chul et al., "Explosive boiling of liquid droplets at their superheat limits", Chemical Engineering Science, 60 (2005) pp. 1809-1821.
Kripfgans, Oliver D. et al., "Acoustic Droplet Vaporization for Therapeutic and Diagnostic Applications", Ultrasound in Medicine and Biology, vol. 26, No. 7, pp. 1177-1189, 2000.
Lo, Andrea H. et al., "Acoustic Droplet Vaporization Threshold: Effects of Pulse Duration and Contrast Agent", IEEE Transactions on Ultrasonics, Ferroelectrics, and Frequency Control, vol. 54, No. 5, May 2007, pp. 933-946.
Noveck, Robert J. et al., "Randomized Safety Studies of Intravenous Perflubron Emulsion. II. Effects on Immune Function in Healthy Volunteers", Anesth Analg, 2000, 91, pp. 812-822.
Campuzano, S.,et al. "Motion-driven sensing and biosensing using electrochemically propelled nanomotors," Analyst 136, 4621-4630 (2011).
Wang, J. "Can man-made nanomachines compete with nature biomotors," ACS Nano 3, pp. 4-9 (2009).
Mallouk, T. & Sen, A. "Powering nanorobots," Sci. Amer. 300, pp. 72-77 (2009).
Castro, Camila Irene et al., "Perfluorocarbon-Based Oxygen Carriers: Review of Products and Trials," Artificial Organs, vol. 34, No. 8, 2010, pp. 622-634.
Le, Thao D. et al., "QSPR and GCA Models for Predicting the Normal Boiling Points of Fluorocarbons", Journal of Physical Chemistry, vol. 99, No. 17, 1995, pp. 6739-6747.
Borkent, Bram M. et al., "The acceleration of solid particles subjected to cavitation nucleation", Journal of Fluid Mechanics, 2008, vol. 610, pp. 157-182.
Wirde, Mikael et al., "Self-Assembled Monolayers of Cystamine and Cysteamine on Gold Studied by XPS and Voltammetry", Langmuir, vol. 15, No. 19, 1999, pp. 6370-6378.
Mezyk, Stephen P., "Rate Constant Determination for the Reaction of Sulfhydryl Species with the Hydrated Electron in Aqueous Solution", Journal of Physical Chemistry, vol. 99, No. 38, 1995, pp. 13970-13975.
Paxton, Walter F. et al., "Motility of Catalytic Nanoparticles through Self-Generated Forces" (Catalytic Movement of Nanoscale Objects), Chemistry European Journal, 2005, 11, pp. 6462-6470.
Lamm, D.L.; Thor et al. "Bacillus Calmette-Guerin Immunotherapy of Superficial Bladder Cancer," J. Urol. 1990, 124: pp. 38-40.
Lamm, D.L. et al. Incidence and Treatment of Complications of Bacillus Calmetter-Guerin Intravesical Therapy in Superficial Bladder Cancer, F.M.; J. Urol. Mar. 1992;147(3):pp. 596-600.

(56) References Cited

OTHER PUBLICATIONS

Kagan et al. "Accoustic Droplet Vaporization and Propulsion of Perfluorocarbon-Loaded Microbullets for Targeted Tissue Penetration and Deformation," Angewandte Chemie Int. Ed. 2012, pp. 7519-7522.
Gao, W. et al. Cargo-towing fuel-free magnetic nanoswimmers for targeted drug delivery. Small (2012), pp. 460-467.
Balasubramanian, S. et al. Micromachine-enabled capture and isolation of cancer cells in complex media. Angew. Chem. Int. Ed. 50, 4161-4164 (2011).

* cited by examiner

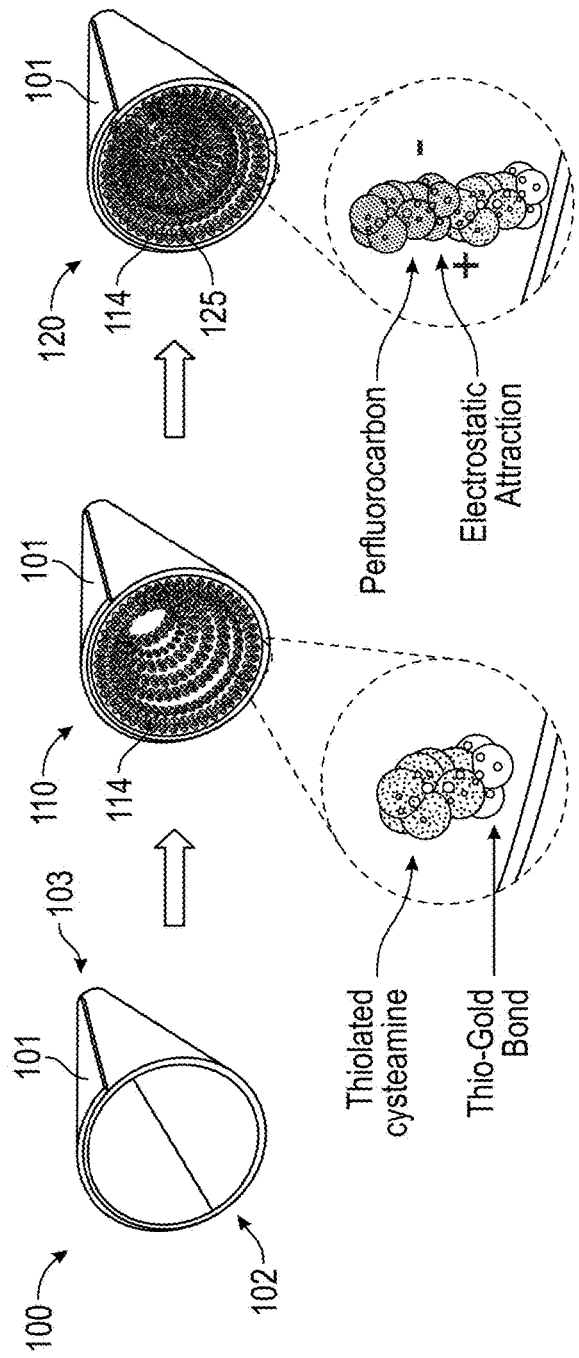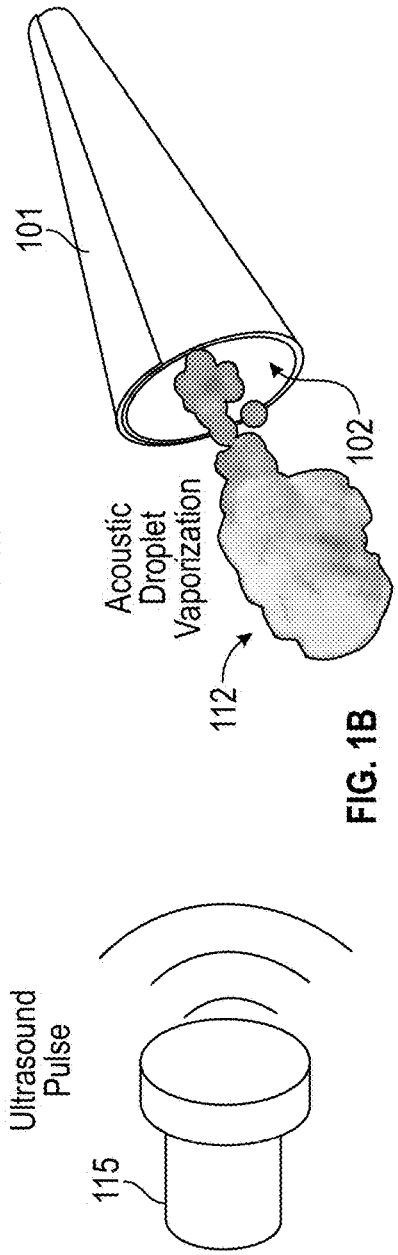
FIG. 1A
FIG. 1B

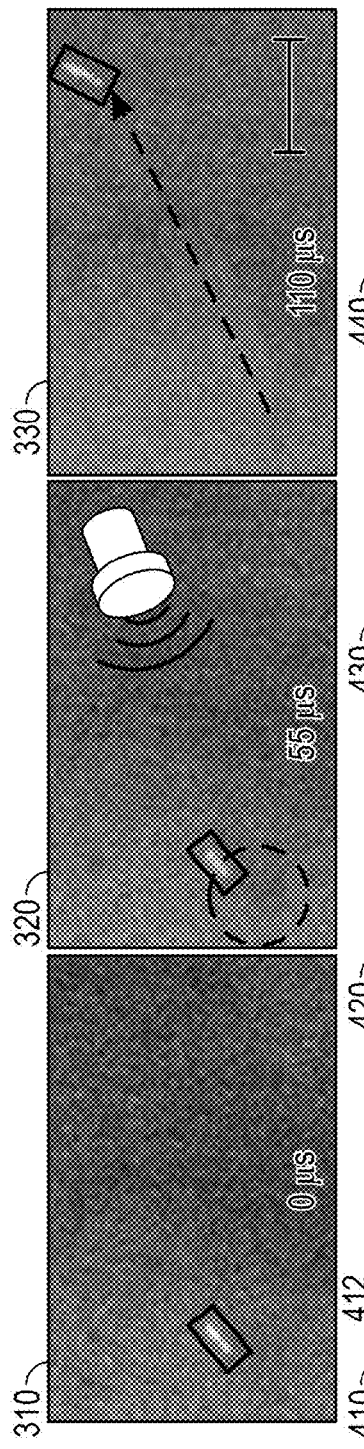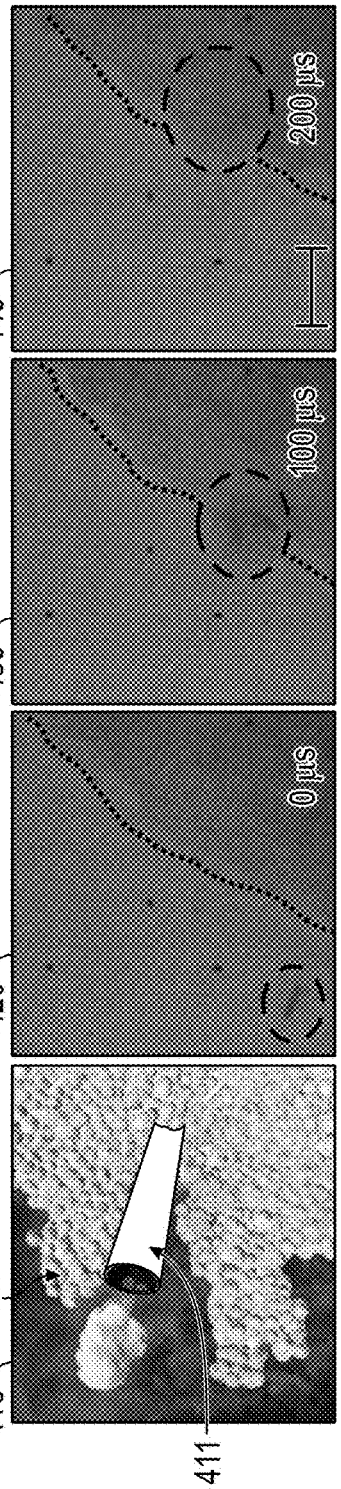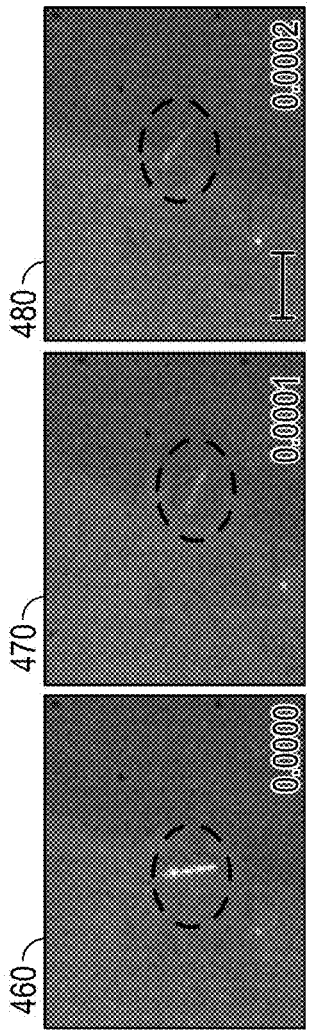

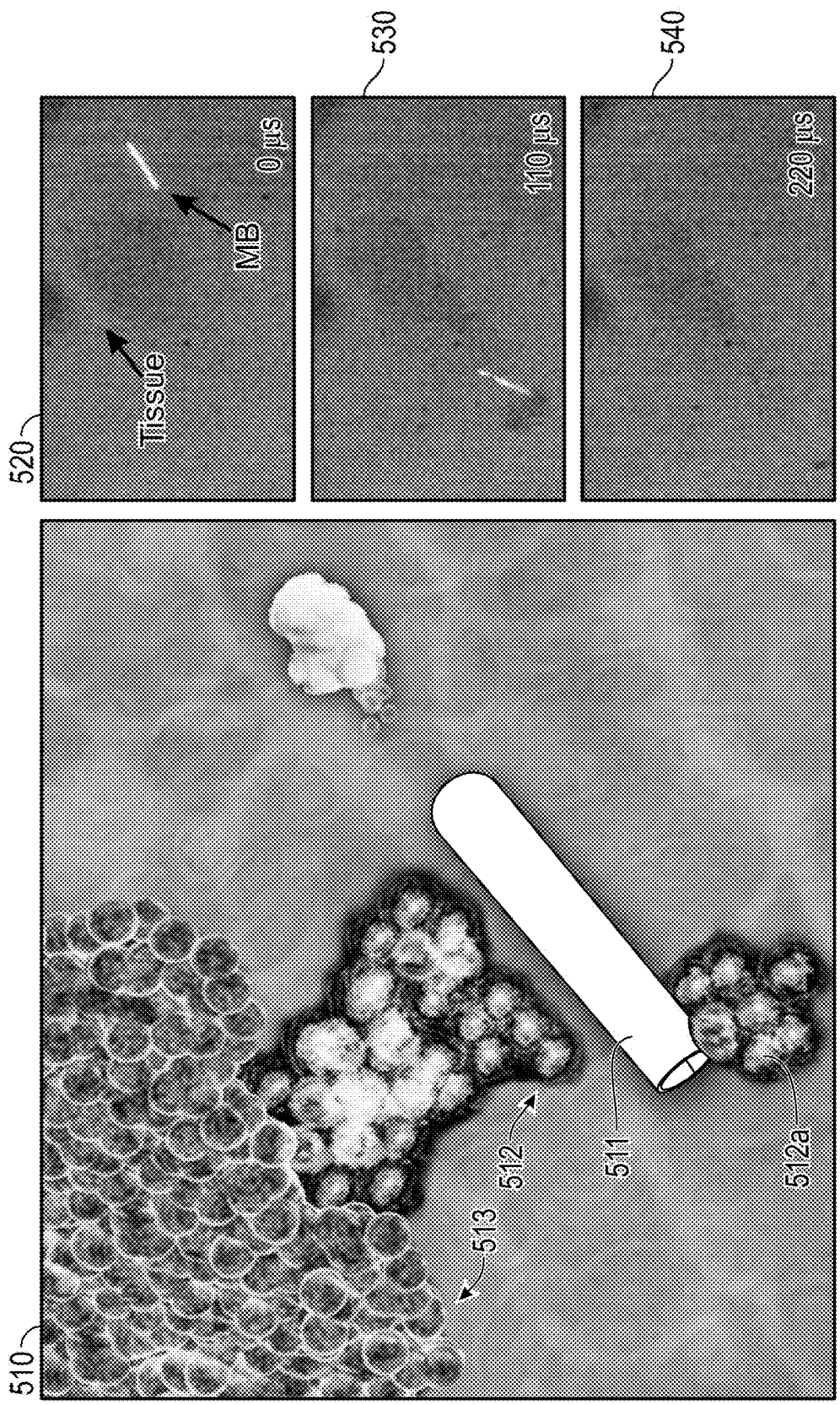

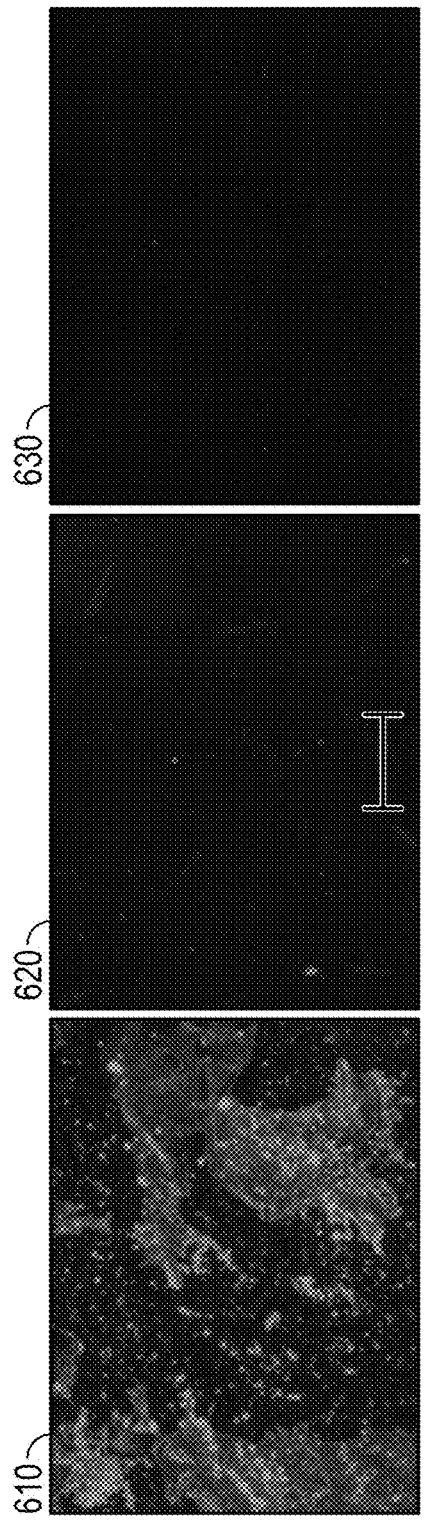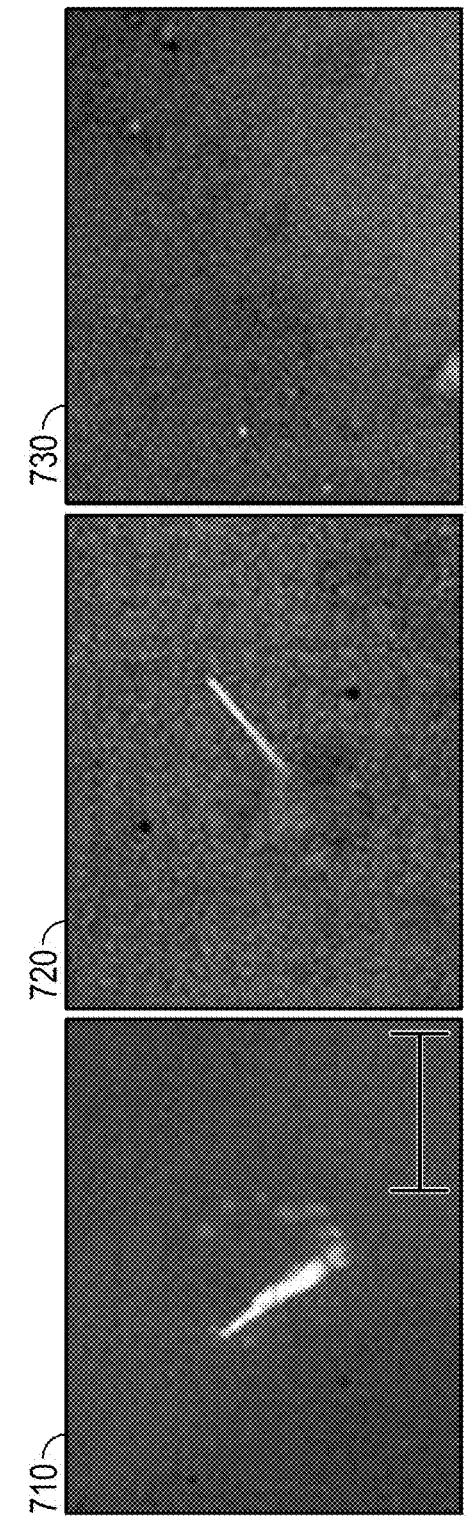
FIG. 6
FIG. 7

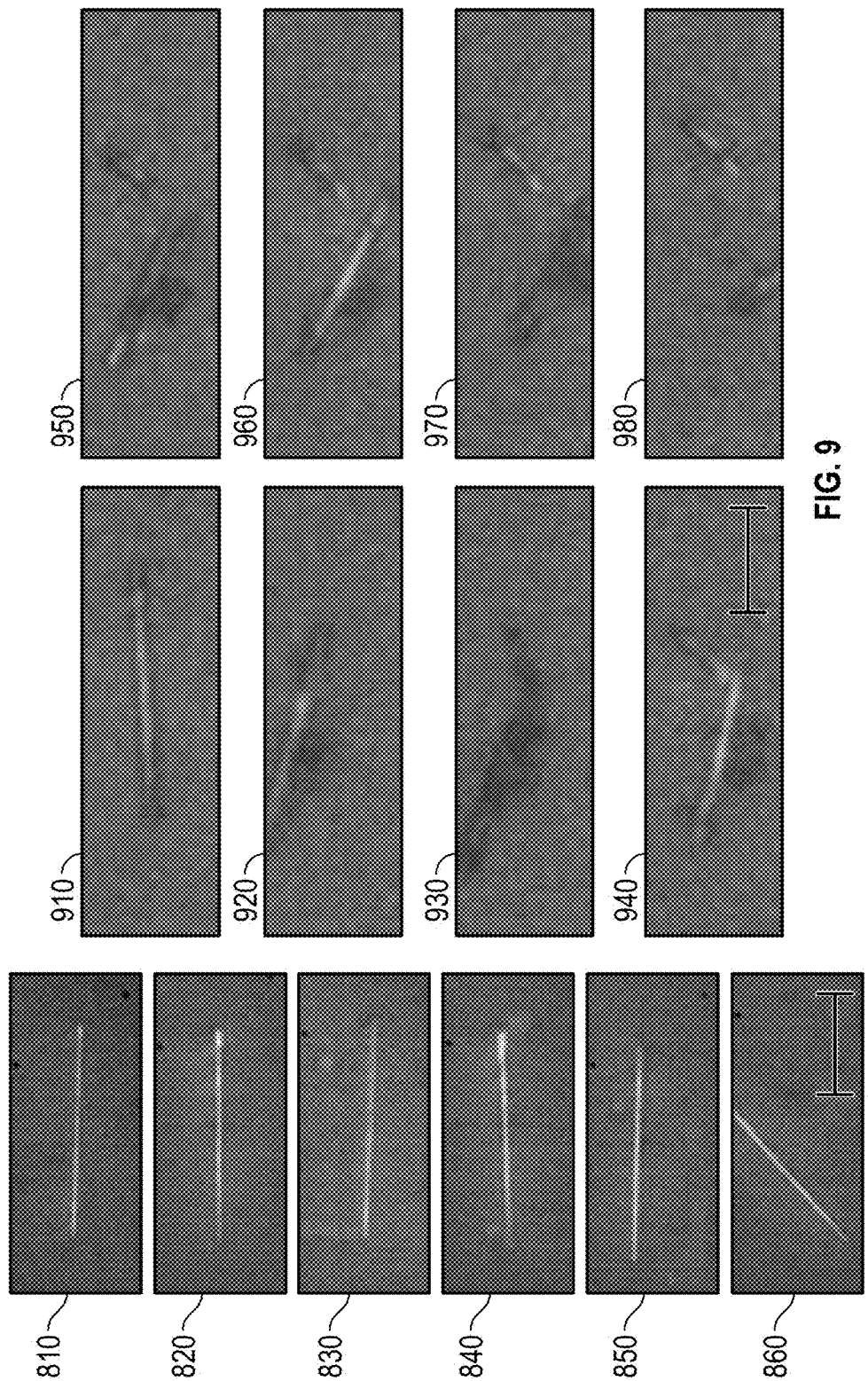

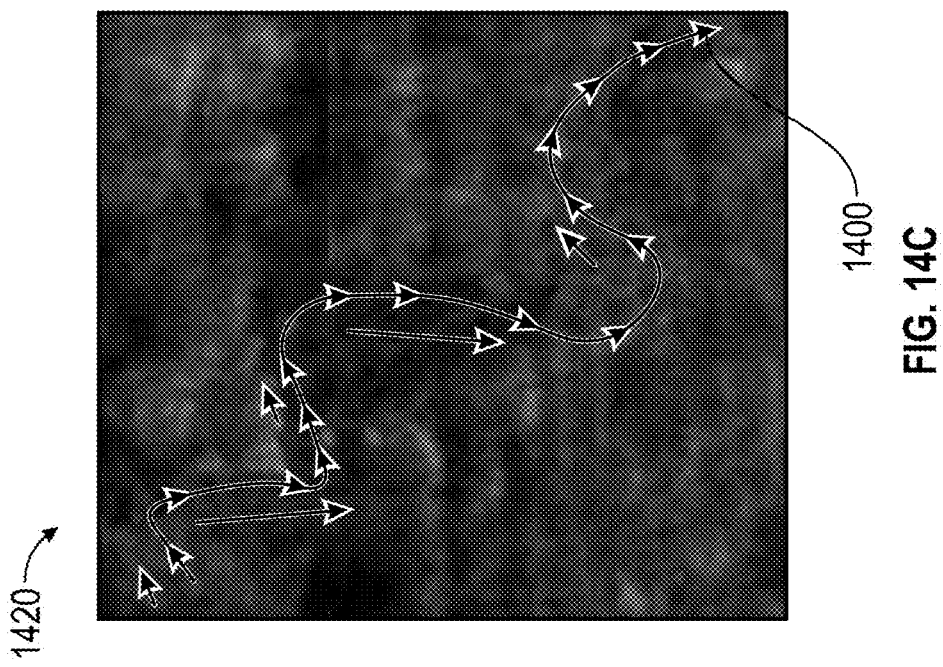
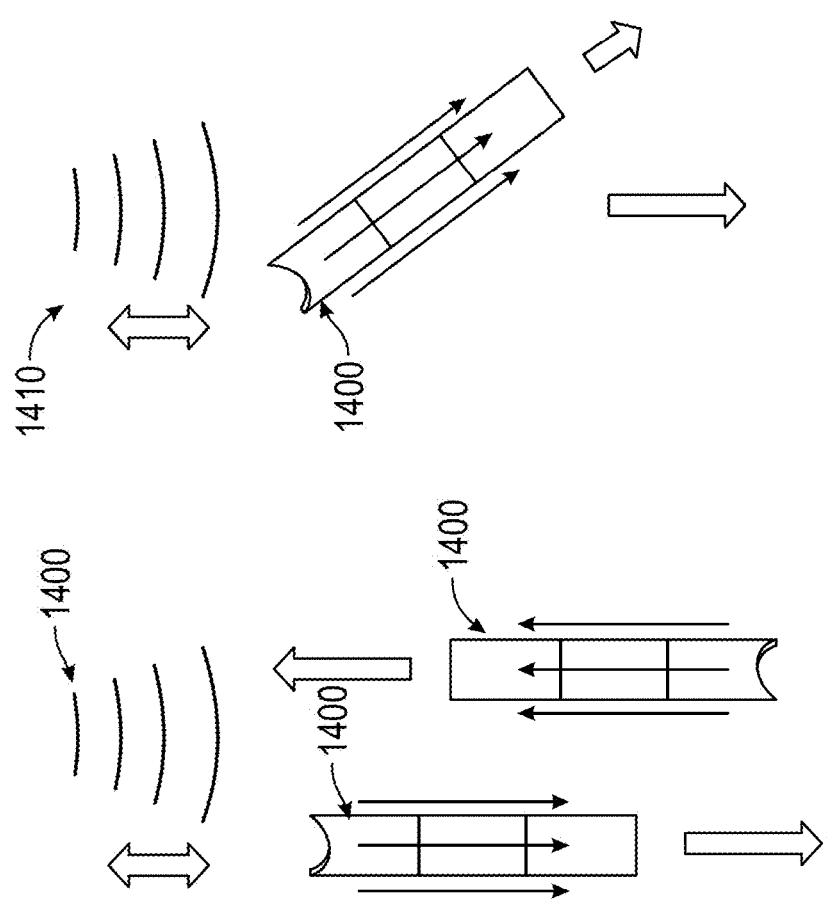
FIG. 14C
FIG. 14B
FIG. 14A

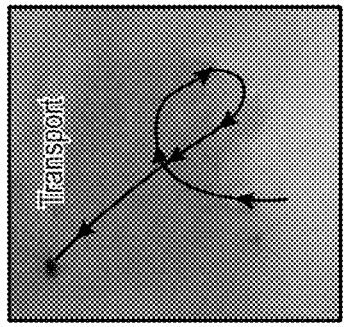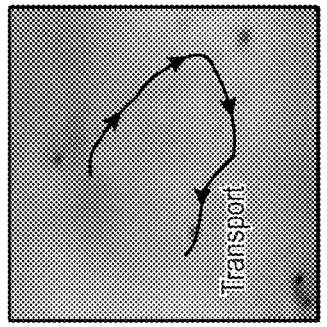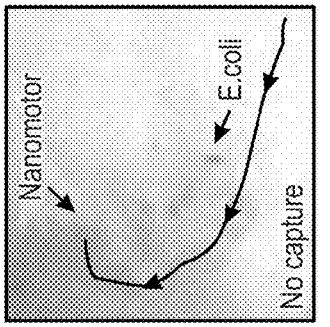
FIG. 16A  FIG. 16B  FIG. 16C
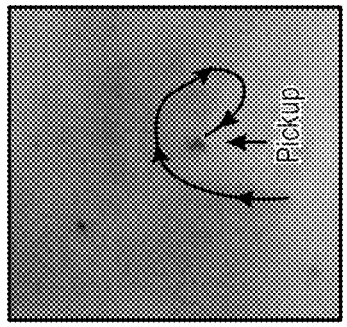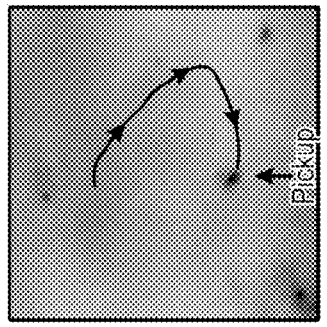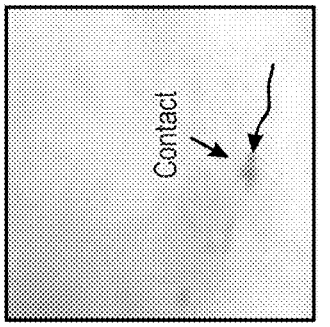
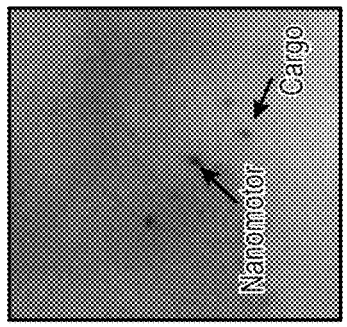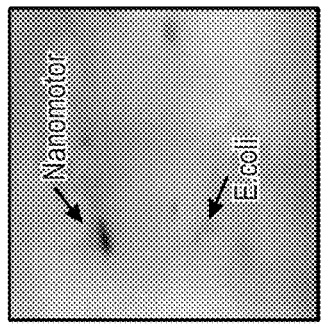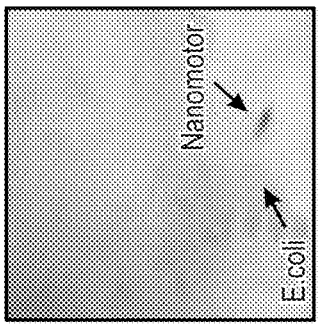
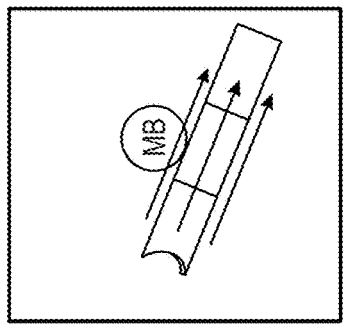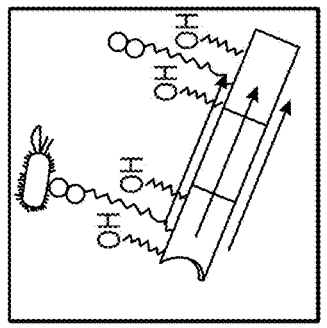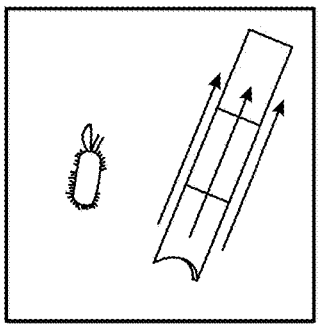

ACOUSTICALLY TRIGGERED NANO/MICRO-SCALE PROPULSION DEVICES

CROSS REFERENCE TO RELATED APPLICATIONS

This application is a 35 USC 371 National Stage application of International Application No. PCT/US2013/026757 filed Feb. 19, 2013, which further claims the benefit of priority to U.S. Provisional Patent Application No. 61/599,825, entitled "ACOUSTICALLY TRIGGERED NANO/MICROSCALE PROPULSION DEVICES," filed on Feb. 16, 2012, the disclosures of which are incorporated by reference as part of this document.

STATEMENT REGARDING FEDERALLY SPONSORED RESEARCH OR DEVELOPMENT

This invention was made with government support under grant CA119335 and CA153915 awarded by the National Institutes of Health (NIH), along with grant CBET 0853375, awarded by the National Science Foundation (NSF). The government has certain rights in the invention.

TECHNICAL FIELD

This patent document relates to micro- and nano-scale technologies including nano particles and nanomotors.

BACKGROUND

Nanotechnology provides techniques or processes for fabricating structures, devices, and systems with features at a molecular or atomic scale, e.g., structures in a range of one to hundreds of nanometers in some applications. For example, nano-scale devices can be configured to sizes similar to some large molecules, e.g., biomolecules such as enzymes. Nano-sized materials used to create a nanostructure, nanodevice, or a nanosystem that can exhibit various unique properties that are not present in the same materials scaled at larger dimensions and such unique properties can be exploited for a wide range of applications.

SUMMARY

The patent document discloses techniques, systems, devices, and materials for acoustically triggered micro/nanoscale propulsion.

In one aspect, an ultrasound responsive propulsion device includes a tube that includes one or more layers including an inner layer having an electrostatic surface, and an ultrasound-responsive substance coupled to the inner layer and configured to form gaseous bubbles in a fluid in response to an ultrasound pulse, in which the bubbles exit the tube to propel the tube to move in the fluid.

In another aspect, an ultrasound system for propelling an acoustically responsive structure includes a mechanism that supplies one or more tubular structures in a fluid medium, the one or more tubular structures each having one or more layers including an inner layer having an electrostatic surface and an ultrasound-responsive substance coupled to the inner layer by electrostatic interaction and configured to form gaseous bubbles in the fluid medium in response to an ultrasound pulse, in which the bubbles exit the tubular structure to propel the tubular structure to move in the fluid medium, and a mechanism that produces ultrasonic acoustic energy and focuses the ultrasonic acoustic energy at a particular region where the one or more tubular structures are located to cause vaporization in the fluid medium at an interface with the ultrasound-responsive substance that triggers the bubbles to form.

In another aspect, a method of using a tubular structure to collect a target substance in a fluid includes supplying a tube in a fluid medium, the tube including an ultrasound-responsive substance on an inner wall of the tube to generate gaseous bubbles in response to ultrasonic acoustic energy, applying an ultrasound pulse to cause vaporization of the ultrasound-responsive substance to form the gaseous bubbles and to propel the tube in the fluid medium, and using a molecular layer on an external surface of the tube to selectively collect a target substance in the fluid while the tube is propelled in the fluid.

In another aspect, a device to locomote in a fluid by acoustic energy includes two or more segments structured to form a rod having an interior cavity spanning from an opening at one end of the rod, in which at least one of the segments includes an outer surface of a modifiable material capable of being functionalized, and in which the rod is structured to interact with an external ultrasound pulse to create a pressure gradient within the interior cavity to propel the device in the fluid.

In another aspect, a method of using a nanowire motor to collect a target substance in a fluid includes supplying a rod in a fluid medium, the rod formed of two or more segments and including an interior cavity spanning from an opening at one end of the rod, applying an ultrasound pulse to create a pressure gradient within the internal cavity to propel the rod in the fluid medium, and using a molecular layer on an external surface of the rod to selectively collect a target substance in the fluid medium.

The subject matter described in this patent document can be implemented in specific ways that provide one or more of the following features. For example, engineered nano/microstructures are actuated in motion within a fluid environment (e.g., such as a biofluids) by using acoustic energy, which provides a biocompatible energy transduction mechanism to power the nano/micromotor structures. For example, the disclosed micro/nanoscale propulsion technology can be implemented in a variety of in vivo and in vitro bioanalytic and biomedical applications including delivery of compounds (e.g., nucleic acids, proteins, other biomolecules, immunostimulatory compounds, or synthetic materials), physical penetration and micro-tissue removal or cleaning schemes, biomolecular/cell sensing and isolation, lab-on-chip cargo transport, and drug delivery targeting, stem cell differentiation and gene therapies, among other applications. The described nano/micromotors possess the ability to accelerate at ultrafast rates and reach average speeds over 6 m/s. The disclosed nano/micromotors can be used to pierce, deeply penetrate, and deform biological tissue, as well as transport tissue samples. For example, the disclosed nano/micromotors can be used to develop small tissue openings and penetrate deep for delivery applications. Implementations of the disclosed technology can provide continuous advancements in targeted delivery schemes (e.g., PLGA/liposomes carriers, virus-encapsulation, stem cell programming, and traditional surgical delivery). For example, exemplary synthetic delivery systems employing exemplary nano/micromotors of the disclosed technology can be made more biocompatible, functionalizable, durable, and predictable than biological systems.

BRIEF DESCRIPTION OF THE DRAWINGS

FIGS. 1A and 1B show illustrations of an exemplary preparation scheme and implementation of an exemplary ultrasound-actuated nanomotor device.

FIG. 3 shows still frame images displaying the trajectory of an exemplary functionalized nanomotor device.

FIGS. 4A and 4B show an exemplary illustration and sequential images of an exemplary nanomotor device penetrating tissue.

FIGS. 5A and 5B show illustrations and images of an exemplary nanomotor device cleaving a diseased tissue section.

FIG. 6 shows images that illustrate exemplary immobilization schemes on Au-sputtered silicon wafers containing rolled-up nanomotor structures.

FIG. 7 shows still frame images displaying bubble emissions from exemplary nanomotor devices after different ultrasound pulses.

FIG. 8 shows still frame images displaying bubble emission from both ends of exemplary large length functionalized nanomotors.

FIG. 9 shows still frame images displaying the breaking of exemplary functionalized nanomotor structures.

FIGS. 14A and 14B show schematic illustrations of the propulsion of exemplary magnetically-steered nanowire motors by ultrasound.

FIG. 14C shows an image showing the trajectory of an exemplary magnetically-guided nanowire motor changing directions.

FIGS. 16A-16C shows a series of images demonstrating the ability of the disclosed magnetically-steered ultrasound-propelled nanomotors to capture and transport a load.

Like reference symbols and designations in the various drawings indicate like elements.

DETAILED DESCRIPTION

Figure 1C:
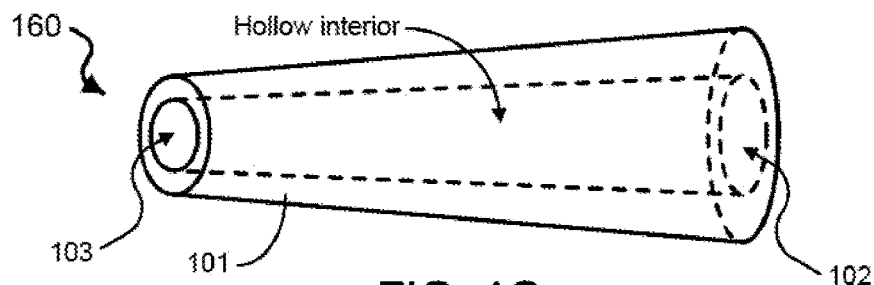
FIGS. 1C-1G show schematics of exemplary ultrasound-propelled nanomotor devices.

This patent document discloses techniques, systems, devices, and materials for controlling motion of nano or micro scale structures such as nano particles and nanomotors, including using acoustic waves to trigger or activate motion of, and propel, nano or micro scale structures in fluid media.

Acoustic waves can exist in a range of acoustic frequencies for their compression and decompression movement traveling through media. Ultrasound refers to acoustic waves operating at frequencies higher than acoustic wave frequencies of the upper level of typical human hearing. Ultrasound signals can be used in biomedical imaging and a variety of other applications including therapeutic purposes. For example, ultrasound waves used in biomedical imaging may operate in different frequencies, e.g., between 1 and 20 MHz, or even higher frequencies. Ultrasound can offer a safe and effective way to externally access deep tissues. For example, ultrasound imaging (also referred to as sonography) is a medical imaging modality that employs the properties of sound waves traveling through a medium to render a visual image of internal structures and functions of animals and humans. Therapeutic applications of ultrasound can include focused ultrasound, which can provide a safe, non-invasive means to deposit energy deep within the body with millimeter precision without causing adverse biological effects.

Nano-/micro-scale structures are disclosed here to utilize a remote source of acoustic energy, e.g., ultrasound waves, to actuate motion of or propel the nano/microstructures in a fluid environment, e.g., independent of the environmental conditions including the pH or chemical make-up of the fluid. In some aspects, the engineered nano/micromotors include an "on board" fuel source, e.g., perfluorocarbon emulsion droplets, loaded onto the structure of the nano/micromotor to vaporize due to ultrasonic waves directed at the nano/micromotors and to accelerate out of the nano/microstructure, propelling the nano/micromotor in the fluid. In other aspects, the engineered nano/micromotors do not include a fuel and instead are propelled in the fluid due to a pressure gradient produced within a hollowed interior of the nano/microstructure by the ultrasound waves penetrating the concave rear end of the nano/micromotors. In some exemplary embodiments of the disclosed nano/microstructures, the structure can be configured in a tubular shape, e.g., including, but not limited to, a cylindrical or conical geometry, in which, for example, one dimension (e.g., such as the diameter of the tube) is in the nanometer regime and another dimension (e.g., such as the length of the tube) is in the micrometer regime. For example, the nano/microstructures can be formed of multiple layers, e.g., having an inner layer formed of a first material and an outer layer formed of a second material or the same material as the first material. In some implementations, for example, the nano/microstructures can include an embedded layer of a magnetic material that permits external guidance for precision steering of the acoustically-propelled nano/micromotor. In some implementations, for example, the inner and/or outer layers can be functionalized to attach other molecules, e.g., such as a fuel substance and/or ligand to interact with a target payload, for example, for capture and transport applications.

The disclosed engineered nano/microstructures may also be referred to in this patent document as nanomotors, nanoengines, nanomachines, nanotubes or nanotube motors, nanocones or nanocone motors, nanowires or nanowire motors, nanorods or nanorod motors, nanobullets, nanorockets, and nano submarines, and/or as micromotors, microengines, micromachines, microtubes, microcones, microwires, microrods, microbullets, microrockets, and micro submarines.

In some implementations, the acoustically-propelled nano/microstructures can be engineered as immuno-nano/micromachines that can isolate target molecules and/or cells from complex samples in vitro and in vivo in a variety of biomedical applications, e.g., including drug delivery to biosensing. For example, the acoustically-propelled immune-nano/micromachines can be configured to move and pick-up/transport payloads in physiological conditions, e.g., within environments having high ionic strength, such as biological fluids. For example, target molecules include, but are not limited to, nucleic acids, lipids, carbohydrates, peptides, proteins, enzymes, hormones, antibodies, glycoproteins, glycolipids, organelles, endotoxins, viruses, and other biological materials and biomarkers. For example, other target payloads can include living organisms such as cells, which include, but are not limited to, healthy cells, cancer cells, bacterial cells, and other types of cells. For example, the disclosed nano/micromotors can propel in a variety of fluids including biological fluids, e.g., such as, but not limited to, aqueous humour and vitreous humour, bile, blood (e.g., blood serum, blood plasma), cerebrospinal fluid, intracellular fluid (e.g., cytoplasm) and extracellular fluid (including interstitial fluid, transcellular fluid, plasma), digestive fluid (including gastric juice and intestinal juice), lymphatic fluid and endolymph and perilymph, mucus (including nasal drainage and phlegm), peritoneal fluid, pleural fluid, saliva, sebum (e.g., skin oil), semen, sweat, tears, urine, vaginal fluids, and bacterial lysates. Other exemplary fluids can include non-biological fluids, such as, but not limited to, pure water, salt-containing water, sugar-containing water, juice, and oil-based fluids.

Nano/micro-scale motors are artificial small-scale structures or devices that can move in a medium by converting energy into motion of the nano/micromotor structure. In some examples, nano/microscale motor technologies can convert external chemical energy, e.g., located within the vicinity of the nano/micromotor, into autonomous propulsion. For example, nano/micromotor devices can include mechanisms to achieve motor thrust by converting a chemical fuel available within the fluid medium to promote propulsion by a mechanism, e.g., including self-electrophoresis, self-diffusiophoresis, and bubble propulsion. As a specific example, hydrogen peroxide can be used as a chemical fuel for such chemically-driven autonomous propulsion of the nano/micromotor devices. Sufficiently high concentrations of hydrogen peroxide fuel may cause issues of toxicity and other detrimental limitations for some nanomotor applications and such issues can limit or restrict such hydrogen peroxide driven autonomous nanomotors in practical biomedical applications e.g., particularly in vivo. Various alternating fuels can be used to power chemically-driven autonomous propulsion of micro/nanomotors. Notably, externally-propelled nano/microscale locomotion schemes can be used to provide fuel-free propulsion mechanisms that, for example, utilize electrical power (e.g., diode nanowires) and magnetic oscillation (e.g., magnetically-propelled nanoswimmers).

Acoustic energy, such as ultrasound, can be focused through tissues and other structures to relatively small volumes inside the tissues or other structures to achieve high energy concentration at the focused locations, e.g., millimeter sized spots and microliter volumes. Examples of existing ultrasound techniques used in biomedical applications include shock lithotripsy, radiation force, high-intensity focused ultrasound, sonoporation, and cavitation. For example, cavitation can include the formation of a gaseous cavity in a liquid due to sudden pressure drops. The formation and collapse of such a cavity is a highly energetic process, e.g., which can produce shockwaves, and in some examples, liquid jets. The use of ultrasound to actuate motion of nanoscale and microscale structures offers promise in several environmental and biomedical applications, as ultrasound waves have minimal deleterious effects on biological and environmental systems. With proper engineering, acoustic energy can be used to produce sufficient thrust of nanomotors or particles for penetrating tissue barriers and cellular membranes for certain applications. Acoustic actuation of nanomotors in biomedical and environmental applications can be implemented by combining proper functionalization of the nanoscale and microscale structures and advanced motion control and cargo-towing capabilities for guidance in relevant media. The acoustic source and associated focusing mechanism may be implemented at locations away from the locations of the nanomotors and thus minimize invasion of, or interference with, the tissues or structures in which the nanomotors are deployed.

In one aspect, the disclosed technology includes nanoscale propulsion devices that utilize acoustic energy (e.g., ultrasound waves) to remotely trigger vaporization of an on-board fuel carried by the nanostructure body to propel the device in a fluid.

For example, the on-board fuel can include perfluorocarbon emulsions bound within the interior of the nanostructure body. Ultrasound waves produced from an external, remote source can generate a pressure explosion of the on-board fuel within the nanostructure body that propels the device. For example, applied acoustic energy, e.g., supplied by the ultrasound waves, cause the exemplary perfluorocarbon molecules packed inside the nanotube body to produce low-boiling point, liquid perfluorocarbon droplets that nucleate to produce gas bubbles. The rapid production and expansion of the nucleated gas creates high pressure within the interior that results in the expulsion of the gas from the nanotube, thereby inducing thrust of the device. Furthermore, an increase in enthalpy which can accompany vaporization results in energy transfer. For example, the exemplary emulsion gases generated during the pressure explosion can cavitate within the interior of the nanotube and the resultant shockwave can add an additional propelling force upon their implosion. Thus, the engineered structure of the disclosed nanomotors can be configured to direct the energy from the particle-nucleated acoustic cavitation events and create net motion of the device. For example, the engineered structure can geometrically focus the momentum of the thrusted nano/micromotor devices to generate projectile motion. Additionally, for example, the structure of the exemplary nanomotors can be configured with an embedded layer of a magnetic material to interact with an externally applied magnetic field used to orient and guide the direction of motion of the acoustically-propelled nanomotors.

Gas and liquid perfluorocarbon (PFC) particles exhibit a biocompatible nature for intravenous injection and subsequent destruction upon ultrasound irradiation. For example, the decreased solubility and low diffusion coefficient of these droplets and bubbles lengthens blood circulation before an incident ultrasound wave is used to induce their destruction or cavitation. PFC can be utilized as an on-board fuel source capable of releasing energy independent of the surrounding environment via an external control (e.g., an acoustic energy source), and thus enabling the utilization of the exemplary nano/micromotors in a variety of in vivo and in vitro biomedical applications.

In some implementations, exemplary nanomotors are configured in a tubular structure with a biocompatible exterior and can accelerate rapidly, reaching ultrafast average velocities (e.g., ~6.3 m/s). For example, the high thrust produced is sufficient for piercing, puncturing, deeply penetrating, deforming, and tearing apart of biological tissue. For example, exemplary implementations are described showing exemplary nanomotors fired into lamb kidney sections. The exemplary nanomotors can be used to interact with a variety of different surfaces. Exemplary implementations demonstrating exemplary nanomotors firing can also be oriented magnetically, and multiple nanomotors can be fired simultaneously and synchronized in motion.

The disclosed technology can be scalable. For example, the fabrication of the nanomotor devices can control size of the nanomotor body and the amount, packing density, and orientation of the on-board fuel (e.g., perfluorocarbon emulsion). For example, the diameter(s) of the opening(s) and/or the length of the nano/micromotor body can be configured in the range from nanometers to millimeters. For example, the shape of the nano/micromotor body can include a variety of geometries and shapes. For example, a variety of materials can be used to fabricate the nano/microstructures. For example, different types of fuels can be utilized to generate the propulsion of the nano/micromotor devices, e.g., on board the device and/or found in the surrounding fluid environment. For example, the external acoustic triggering source can be configured to actuate the nanomotor devices in a variety of different amplitude and frequency settings. Additionally, for example, other external forces (e.g., heat, radiation, among others) can be used to promote fuel excitement and subsequent propulsion.

Exemplary fabrication methods and exemplary implementations demonstrating the functionality and efficacy in a variety of applications are described. For example, the disclosed acoustically-triggered nanomotors can be deployed safely and deep into biological tissue. Exemplary in vivo applications of the disclosed technology include drug delivery, artery cleaning, biomolecular/cellular delivery, tissue sampling, crossing the blood/brain barrier, tissue penetration for triggering immune responses and/or targeted gene regulation schemes. Exemplary in vitro applications of the disclosed technology include cell or tissue penetration, deformation, and delivery applications.

FIGS. 1A and 1B show schematic illustrations of the fabrication and implementation of exemplary ultrasound-propelled nano/micromotor devices. FIG. 1A shows a schematic 100 illustrating the process to fabricate the nanostructure body 101 of an exemplary nanotube motor device. In some implementations, the fabrication process can include a top-down photolithographic procedure involving angled e-beam evaporation to provide stress-assisted rolling of functional nanoscale membranes (e.g., on a polymer substrate) to form multilayered conical nanotubes. The exemplary conical nanotube body structure 101 in schematic 100 can be configured as a tube structured to include a large opening 102 and a small opening 103 that are on opposite ends of the tube, in which the nanostructure body 101 connects the large and small openings 102 and 103 and has a cross section spatially reducing in size along a longitudinal direction from the large opening 102 to the small opening 103. For example, the nanostructure body 101 can be formed of multiple layers, e.g., having an inner layer formed of gold and an outer layer formed of a second material, e.g., such as platinum, or the same material as the inner layer material (e.g., gold). For example, the multiple layers of the nanostructure body 101 can include an embedded layer of a magnetic material that permits external guidance for precision steering of the nanomotor device. FIG. 1A shows a schematic 110 illustrating the process to functionalize the hollowed interior of the nanotube body 101 with a linker substance 114. In some implementations, the inner layer of the nanostructure body 101 includes gold, and the linker substance 114 can include a thiolated alkane chain molecule with a cysteamine functional group terminus. For example, the inner Au layer can facilitate the conjugation of the exemplary cysteamine-terminated thiolated monolayer (e.g., via thiol-gold interactions) in the interior of the nanostructure body 101, as shown in the inset illustration of the schematic 110. FIG. 1A further shows a schematic 120 illustrating the process to bind a chemical fuel substance 125 to the nanostructure body 101 of the nanomotor device using the linker substance 114 as the intermediary. In some implementations, the chemical fuel substance 125 can include an anionic perfluorohexane emulsion that electrostatically binds to the positively charged cysteamine-functionalized interior surface of the device, as shown in the inset illustration of the schematic 120.

FIG. 1B shows a schematic illustration of the propulsion of the exemplary nanomotor device actuated by ultrasound pulses from an ultrasound wave source 115. As shown in the illustration, the ultrasound pulses from the source 115 trigger the rapid expansion and vaporization of perfluorocarbon droplets in the interior of the nanostructure body 101 of the nanomotor device. This process is referred to as acoustic droplet vaporization (ADV). Bubbles 112 are formed by ADV and are expelled from the nanostructure body 101 from the large opening 102, e.g., due to pressure within the interior, which propel the nanomotor device to move in a fluid medium (e.g., such as a biological fluid). The tapered conical structure of the nanomotor device directs the thrust generated from ADV, while an exemplary embedded magnetic layer allows for externally-guided, magnetic steering of the nanomotor device. For example, both the structure and composition of the nanomotor device lead to the power and control that facilitate an attractive pathway for targeted tissue penetration and deformation of biological tissue. For example, the resulting ultrasound-driven nanomotor devices possess remarkable energy and penetrative force for tissue and cellular penetration. For example, the ability of ultrasound to externally access deep tissue, as well as the history of safe and effective use of ultrasound clinically, and combined with the biocompatible nature of the exemplary PFC emulsions, create a propulsion mechanism well-suited for in vivo applications.

FIGS. 1C-1G show schematics of exemplary ultrasound-propelled nanomotor devices showing various shapes and geometries of the nanotube structure body and openings. FIG. 1C shows an exemplary nanomotor device 160 configured in a conical structural configuration of the nanostructure body 101. The exemplary nanomotor device 160 is structured to include a hollowed interior between the large opening 102 and the small opening 103. The hollowed interior of the exemplary nanomotor device 160 includes a cross section spatially reducing in size along a longitudinal direction from the large opening 102 to the small opening 103.

Figure 1D:
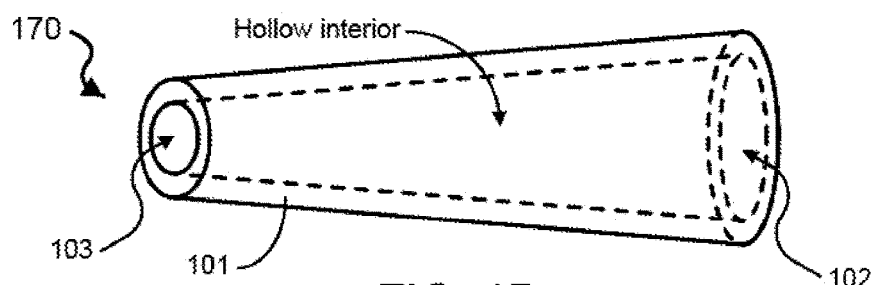

FIG. 1D shows an exemplary nanomotor device 170 configured in a conical structural configuration of the nano structure body 101 with a relatively larger opening size of the opening 102 than that of the exemplary nanomotor 160. Thus, the exemplary nanomotor device 170 includes a larger spatially reduction of the hollowed interior's cross section along the longitudinal direction from the large opening 102 to the small opening 103 as compared to that of the exemplary nanomotor device 160.

Figure 1E:
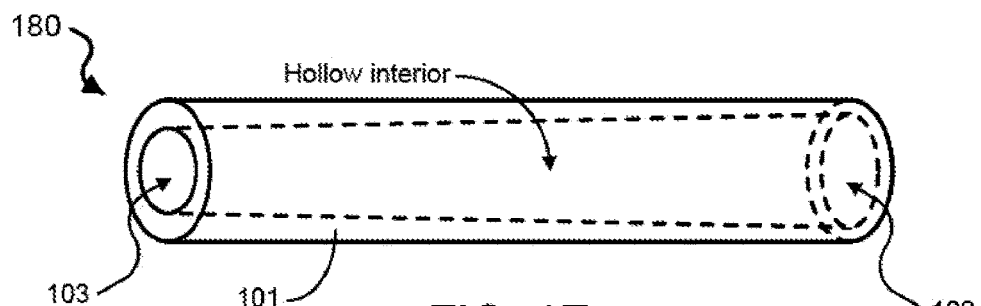

FIG. 1E shows an exemplary nanomotor device 180 configured with a cylindrical exterior structure of the nanostructure body 101 with a hollow conical interior. The hollow conical interior is structured between the large opening 102 and the small opening 103. The hollow conical interior of the exemplary nanomotor device 180 includes a cross section spatially reducing in size along the longitudinal direction from the large opening 102 to the small opening 103.

Figure 1F:
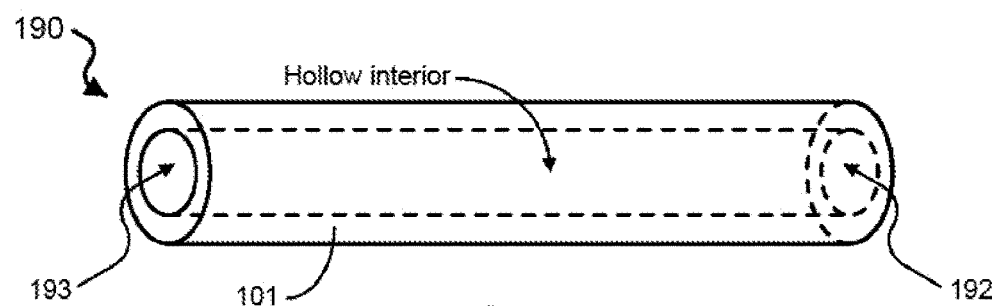

FIG. 1F shows an exemplary nanomotor device 190 configured with a cylindrical exterior structure of the nanostructure body 101 with a hollow cylinder interior. The hollow cylindrical interior is structured between the opening 192 and 193, e.g., each having a diameter substantially equal in length. The hollow conical interior of the exemplary nanomotor device 190 includes a cross section homogeneous in size along the longitudinal direction between the openings 192 and 193.

Figure 1G:
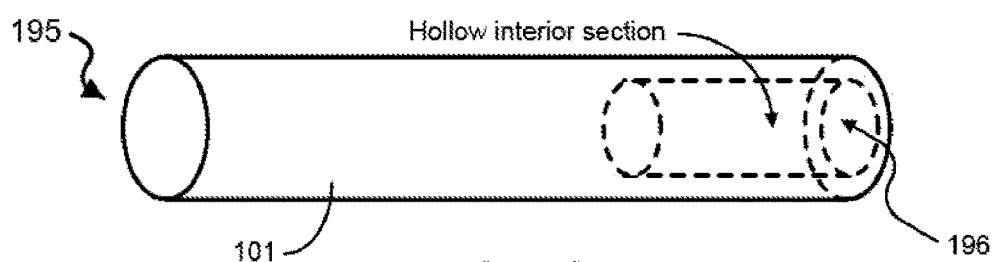

In some examples of the disclosed nanomotor devices, the nanostructure body 101 may including only one opening structured to include a concave hollowed interior along the longitudinal direction configured to a particular distance. FIG. 1G shows an exemplary nanomotor device 195 configured with a cylindrical exterior structure of the nanostructure body 101 with a hollow interior section. The hollow interior section projects from an opening 196 at one end of the nanostructure body 101. In the example shown in FIG. 1G, the hollow interior section is configured in a cylindrical shape. In other examples, the hollow interior section of the nanomotor device 195 can be configured in other shapes, e.g. including, but not limited to, a conical shape, a hemispherical shape, and a faceted shape, among others.

Exemplary ultrasound-propelled fuel-loaded nanomotor devices were utilized in exemplary implementations described herein. Methods of fabrication of these exemplary nanomotors and conditions of their implementations are disclosed.

In some implementations, the exemplary nanomotors were fabricated to include a desired length (e.g., 40 μm). For example, the nanostructure body can be formed of three layers including an outer Ti layer, a middle (embedded) Ni layer, and an interior Au layer. The multilayered Ti/Ni/Au nanostructures configured of a 40 μm length were prepared by a top-down photolithographic process, which involved angled e-beam evaporation to provide stress-assisted rolling of functional nanomembranes on polymers to form a conical nanotube structure. The process first includes spin-coating a positive photoresist (e.g., positive microposit S1827 photoresist, Microchem, Newton, Mass.) onto a silicon wafer, e.g., at 3000 rpm for 60 seconds. The coated wafer can be baked (e.g., for 60 seconds at 115° C.) before UV light exposure (e.g., 35 seconds) using a mask aligner (e.g., MA6 mask aligner) and various-sized nanomotor patterns. For example, the exposed patterns can be etched using a MF-321 developer for 90 seconds before washing thoroughly with DI water. The process includes sequentially evaporating metallic layers of Ti (e.g., 10 nm), Ni (e.g., 15 nm), and Au (e.g., 15 nm) onto the wafer to form the tubular nanostructures, e.g., of 40 and 60 μm length and diameters of openings in the size range 40-300 μm, using an e-beam evaporator (e.g., Temescal BJD 1800) under high vacuum conditions (e.g., <$10^{-8}$ Pa). For larger nanomotor devices (e.g., >100 μm), for example, thicker layers (e.g., 20 nm of Ni and Au layers) can be deposited to provide needed support. In some implementations of the exemplary fabrication process, the e-beam substrate holder was tilted to 48° in all cases to asymmetrically deposit the metals on the patterns. Resist remover, e.g., MF-1165 resist remover (Rohm & Haas, Marlborough, Mass.), was applied to the pre-stressed metallic layers, allowing for the immediate self-assembly of nanotubes. Additionally, for example, the exemplary fabrication process can include critical-point drying of the nanotube structures to prevent unwarranted tubular collapse.

In some implementations, the exemplary nanomotors were fabricated to include a length of substantially 8 μm. The 8 μm length multilayered nanostructures having an outer polyaniline (PANI) layer and an inner Au layer were prepared by electrodepositing sequential layers into a cyclopore polycarbonate membrane, e.g., containing numerous 2 μm conical-shaped pores (e.g., such as that of Catalog No 7060-2511; Whatman, Maidstone, U.K.). For example, electrodeposition of an outer PANI layer and an inner Au layer can be carried out using a three-electrode set-up. For example, PANI nanotubes can be electropolymerized at +0.80 V for 0.02 C from a solution containing 0.1 M $H_2SO_4$, 0.5 M $Na_2SO_4$ and 0.1 M aniline. Subsequently, the inner gold layer can be plated at −0.9 V for 1 C from a gold plating solution (e.g., such as Orotemp 24 RTU RACK; Technic Inc.). The membrane can be dissolved in methylene chloride and repeatedly washed in methylene chloride, ethanol and ultra-pure water. Electron beam evaporation of a 10 nm Ti layer (e.g., to serve as an adhesion layer) and a 26 nm Ni intermediate layer (e.g., providing the magnetic layer for steering) onto the dried PANI/Au nanostructure can be used to magnetically orient the small exemplary 8-μm-long multilayered nanostructures.

In some implementations, the exemplary nanomotors were functionalized to include a perfluorocarbon emulsion along the interior surface of the nanotube structure. For example, perfluorohexane (PFH) droplets, which possess a low boiling point temperature (e.g., 56° C.), were utilized as they maintain stability under physiological conditions but enable ADV upon arrival of incident ultrasound pressure waves. For example, perfluorohexane and perfluoropentane nanoemulsions can be prepared in phosphate buffer saline (PBS). For example, 10 μL of 1 mM DiI-C18 (Biotium, Hayward, Calif.) dissolved in chloroform can be evaporated in a 1.5 microcentrifuge tube. For example, 850 μL of PBS can be added to the solution and a XL-2000 probe-type sonicator (Misonix, Farmingdale, N.Y.) can be operated at the bottom of the tube (e.g., at level 20) until the exemplary DiI film is completely suspended in the buffer and the solution becomes hot to the touch. For example, the tube can be heated in a heating block at 90° C. for 5 minutes, and 50 μL of Zonyl FSE (Wilmington, Del.) anionic fluorosurfactant was added. The solution can be vortexed until homogenized and subsequently cooled in an ice bath. For example, an 100 μL aliquot of perfluoropentane (Strem Chemicals, Newburyport, Mass.) or perfluorohexane (Alfa Aesar, Ward Hill, Mass.) can be added and an XL-2000 probe (Misonix, Farmingdale, N.Y.) can be lowered in the tube about 8 mm from the bottom. While still in the ice bath, the sonicator can be operated with a LabVIEW program interfaced with the sonicator via a foot pedal input and a reed relay board. For example, in some implementations, the program delivered three 0.5 second bursts and was repeated 60 times. The short bursts prevented the solution from stirring violently and producing foam; a 15 sec delay between each set of three bursts served to prevent overheating. The exemplary result is a 10 vol % PFC emulsion that is stable and turbid in appearance. Emulsion sizes and zeta potentials can be measured by dynamic light scattering, e.g., with a Zetasizer Nano-ZS (Malvern Instruments, Worcestershire, UK). The 10 vol % PFC emulsion can be diluted to 1% vol % by a PBS solution (e.g., pH 7.4) before incubating with the exemplary fabricated nanomotor structures.

Exemplary conjugation methods to attach the exemplary perfluorocarbon emulsion to the exemplary nanostructure interior are described. For example, the inner Au layer allows electrostatic binding and selective localization of the perfluorocarbon emulsions to the inner cavity of the nanostructure. Thus, for example, bubbles can be formed within and emitted from the nanomotor devices during ultrasound pulses. The exemplary Au interior layer provides an optimum surface for direct cysteamine binding, e.g., such as that shown in the schematic 110 in FIG. 1A, thereby forming a densely packed monolayer, e.g., within 5 minutes. The exposed amine group (e.g., pKa 8.6) of the cysteamine functional group of the linker monolayer 114 is positively charged for the prescribed settings (e.g., pH range 7.4-8.0), and thus electrostatically binds to emulsions stabilized with an anionic phosphate fluorosurfactant (e.g., pKa 7.2). In such exemplary implementations, emulsions were strongly negative with a measured zeta potential of −46 mV in PBS.

For example, before the electrostatic emulsion binding, copious amounts of DI water can be used in numerous washing steps (e.g., ~15) to remove all excess cysteamine. For example, to ensure optimal emulsion binding for sufficient nanomotor propulsion, the nanomotor structures can be incubated overnight within the perfluorohexane emulsion under continuous flat shaker agitation (e.g., 400 rpm). The exemplary nanomotor structures can be repeatedly washed (e.g., 10 times) with PBS/ultra-pure $H_2O$ (e.g., 1:1000; final pH 8.0) before utilizing the nanomotors. This exemplary composition of the washing solution prevents the nanostructures from electrostatically binding to the glass surface while still promoting the emulsion/nanostructure interaction. In some implementations of the functionalization process, for example, saturation with liquid perfluorohexane (non-active) can be used to prevent dissolution of the bound emulsion while stored for several days before implementation. In some examples, fluorescently-labeled perfluorohexane emulsions were used on a top metal surface of a gold-sputtered silicon wafer to reveal the selective binding of perfluorohexane only in the presence of cysteamine. Other functionalization processes, e.g., such as, but not limited to, electrostatic or covalent linking may be can used to bind the internal fuel source.

Exemplary implementations showing the propulsion of the fabricated and functionalized nanomotors were performed. For example, ultrasound signals were generated by a Panametrics V305-SU (Olympus NDT Inc., Waltham, Mass.), 2.25 MHz transducer connected via a Panametrics BCU-58-6 W waterproof connector cable. The transducer was positioned within a water tank while the nanomotors were positioned at the water surface level between a glass slide and cover slip. For example, the glass slide acted as a coupling medium between the water tank and the nanomotors for the ultrasound pulses. Distinct ultrasound waveforms were generated from a PCI-5412 arbitrary waveform (e.g., National Instruments, Austin, Tex.) and amplified by a 300 W amplifier (Vox Technologies, Richardson, Tex.) to create acoustic intensities of up to 3 MPa peak negative pressure at the focus. An exemplary custom-designed LabVIEW 8.2 program was utilized to initiate the ultrasound pulses while a Photron FASTCAM 1024 PCI acquired the image sequences. A 40× magnification lens was used to acquire most initial images to visualize the gaseous bubbles; a 10× magnification lens was used to observe the nanomotors' locomotion and tissue penetrating characteristics. The glass slide acted as a coupling medium between the water tank and the nanomotors for the ultrasound pulses. In some implementations, for example, in order to reduce the nanomotors' velocity for improved imaging, 20% v/v glycerol was added to the nanomotors solution to increase viscosity (e.g., as shown later in FIG. 3). Imaging during the exemplary implementations included still photo and video capture of the acoustically-actuated nanomotor propulsion devices. For example, individual image frames were acquired at 10,000 or 18,000 frames per second (fps) using a (10×, 20× or 40× objective) FASTCAM 1024 PCI high speed camera (e.g., Photron, San Diego, Calif.). This exemplary acoustically-triggered setup is just an example and many alternative acoustically triggered setups can be used to obtain nano/microscale propulsion.

Figure 2:
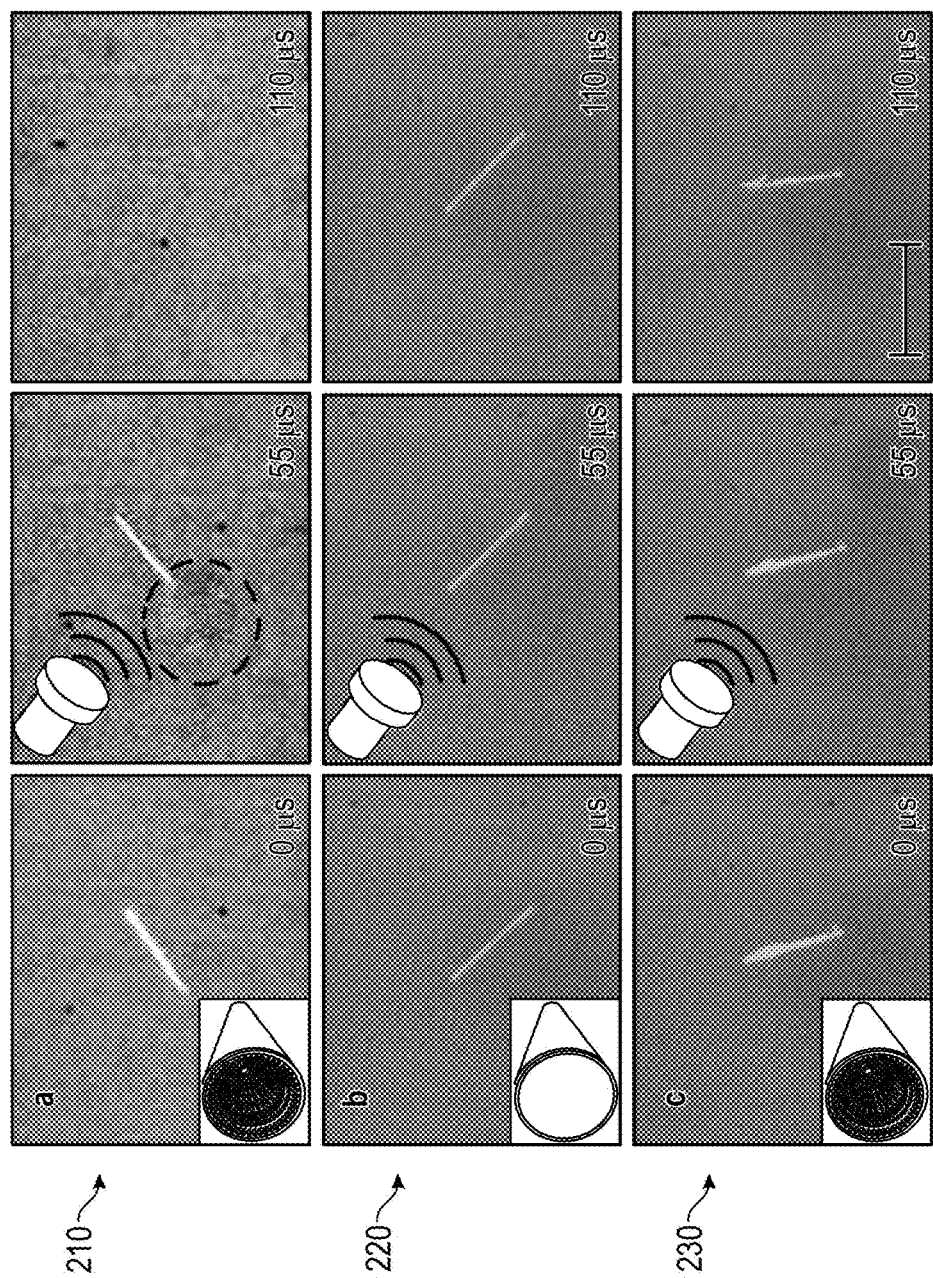
FIG. 2 shows exemplary images and illustrations demonstrating ultrasound-triggered nanomotor propulsion.

FIG. 2 shows three panels of images with illustrations demonstrating ultrasound-triggered propulsion of exemplary 40 μm long nanomotors. The panel of images 210 shows an exemplary fully-modified nanomotor structure, e.g., conjugated with cysteamine and containing perfluorohexane emulsion droplets within the hollow interior of the nanostructure. The panel of images 220 shows an exemplary non-functionalized nanomotor structure, e.g., without cysteamine, but after emulsion incubation, in which no PFC conjugates to the hollow interior of the nanostructure. The panel of images 230 shows another exemplary non-functionalized nanomotor structure, e.g., conjugated with cysteamine but without emulsion incubation. The panels of images 210, 220, and 230 of FIG. 2 include three still frame images of the respective nanomotors before, during, and after a single ultrasound triggering (e.g., 44 μsec, 1.6 MPa ultrasound pulse), in which the before, during, and after images are shown from left to right. Inset illustrations are included in each panel of images 210, 220 and 230 showing the interior region of the respective nanomotor structures illustrating the modification. The still frame image taken during the ultrasound pulse (middle image) in the panel 210 includes an exemplary yellow dotted circle around the emerging bubbles produced by the fully-modified nanomotor during ultrasound-actuated propulsion. The exemplary images were taken at a frame rate of 18,000 fps using a 40× objective. An exemplary scale bar is shown representing 40 μm of all presented images in FIG. 2.

For example, as shown in the panel of images 210 in FIG. 2, a vaporized emulsion (e.g., bubbles) extending out of the rear, large opening of the nanomotor structure is clearly visible after the ultrasound pulsation. The formation of a large microscale bubble is the result of the sudden ultrasound-promoted perfluorohexane emulsion vaporization into a spherical microscale gaseous bubble. Both the rapid emulsion expansion during the vaporization process and the subsequent microbubble implosion provide a sudden impulse that projects the nanomotor out of the field of view within 1/18000 second. For example, the rapid emulsion expansion during the vaporization process (e.g., ~5 fold radial) provides a sudden impulse that projects the nanomotor out of the microscope field of view within an extremely short single image frame (~55.6 μs). In contrast, the panels of images 220 and 230 show the exemplary nanomotors lacking cysteamine modification (panel 220) and lacking emulsion incubation (panel 230), which failed to produce neither bubbles nor substantial movement for the single ultrasound pulse triggering. In conducted tests, the single ultrasound pulsation had a minimal effect on the locomotion of non-functionalized nanomotors, but was sufficient in triggering propulsion of the exemplary fully-modified nanomotor structure.

In order to enhance the visualization of nanomotor movement for subsequent analysis, the nanomotors were viewed under a low magnification lens (10×) and at times placed in a viscous solution (e.g., containing 20% v/v glycerol). FIG. 3 shows a panel of still frame images 310, 320, and 330 displaying the trajectory of an exemplary nanomotor functionalized with PFH emulsion using still frame images (e.g., 1/18000 s frame time; 10× objective) before and after a 44 μsec, 1.6 MPa ultrasound pulse. Image 310 displays the initial position of the exemplary fuel-functionalized nanomotor before the ultrasound pulse. Image 320 shows the motion of the exemplary fuel-functionalized nanomotor after the ultrasound pulse. The image 320 shows while a bubble cloud that is emitted from the rear (larger) opening, e.g., shown in the yellow dotted circle. Image 330 shows subsequent movement of the exemplary fuel-functionalized nanomotor, e.g., visualized using red trajectory line superimposed over the image. For example, an orange box tracks the nanomotor movement, and an exemplary ultrasound triggering illustration was added for clarity. The exemplary scale bar represents 300 μm.

For example, as demonstrated in FIG. 3, the exemplary fuel-functionalized nanomotor is propelled by the vaporization of the emulsion and cavitation of a gas bubble (as shown by the yellow ring in the image 320). FIG. 3 depicts the nanomotor locomotion over a series of three frames in which the nanomotor travels 350 μm from its initial location within 55.6 μs upon vaporization of the PFH emulsion and formation of a gas bubble. Therefore, the exemplary fuel-functionalized nanomotor traveled at a remarkably high average velocity of 6.3 m/s, corresponding to an ultrafast relative velocity of over 158,000 body-lengths/s, and forces in the micro-Newton range (e.g., ~5.15 μN).

The nanomotor dynamics were analyzed with Stokes' Law and image analysis techniques. The initial nanomotor velocity (e.g., 56.9 m/s), kinetic energy (e.g., 0.764 nJ) and momentum (e.g., 2.69×10$^{11}$) were calculated with Equations (1)-(3) in conjunction with nanomotor parameter values presented in Table 1 (shown later in the patent document).

$$v_0 = \frac{\Delta d}{\frac{m}{k}\left(1 - \frac{m}{k}e^{-\frac{k\Delta t}{m}}\right)} \quad (1)$$

$$E_k = \frac{1}{2}mv^2 \quad (2)$$

$$p_0 = mv_0 \quad (3)$$

In the Equations (1)-(3), k is the drag coefficient for a cylinder, m is the mass of the hollow nanomotor (kg), Δd is distance traveled (m), t is time (s), and $E_k$ is kinetic energy (J). For example, the high initial and average nanomotor velocities associated with ultrasound-triggered emulsion vaporization compare favorably with velocities achieved for stochastically moving microparticles propelled by water cavitation. Also, for example, the motor's size, shape, fuel and the ultrasound pulse length and power can be varied to cause the nanostructure to travel farther, bubble from both sides, travel circularly, in 3 dimensions or even explode.

The velocity of the nanomotor locomotion was calculated via Stokes' Law. With the observations of the nanomotor motion, and the Stokes' drag law for cylinders, it is possible to calculate many key physical parameters, e.g., such as:

$$F = \frac{2\pi\mu L}{\ln\left(\frac{2L}{R}\right) - 0.72} v \quad (4)$$

$$F_d = kv \quad (5)$$

where $$k = \frac{2\pi\mu L}{\ln\left(\frac{2L}{R}\right) - 0.72},$$

and μ is the viscosity of the medium, L is the length, R is the radius, and v is the velocity. For example, using values from the Table 1 (below), the average speed is 6.3 m/s determined from the distance traveled of 350 μm in 1/18,000 seconds (time elapsed in one frame). For example, using this calculated velocity in the Stokes' drag law for cylinders, the average drag force is determined to be 50.6 μN. For example, to calculate the initial impulse of the ultrasound triggered propulsion, initial nanomotor's speed and metal mass (e.g., negating the inner air/liquid containing volume) were evaluated to determine the instantaneous change in momentum.

TABLE 1

| Velocity Components | Values |
| --- | --- |
| Average Density | 11.7 g/cm$^3$ |
| Pre-rolled Volume (L × W × T) | (40 × 25 × .04 μm) = 4.00 × 10$^{-11}$ cm$^3$ |
| Mass | 4.74 × 10$^{-13}$ kg |
| Solution Viscosity | 1.05 cP |
| Radius Rolled Nanomotor | 2.5 μm |
| Time Between Frames | 1/18000 s |
| Distance Traveled | 350 μm |
| Drag Coefficient | 8.89 × 10$^{-8}$ |

The equation for the change in velocity over time (acceleration) was utilized to calculate the initial nanomotor velocity $$\frac{dv}{dt} = -\frac{F_d}{m} = -\frac{kv}{m},$$

where m is the mass of the nanomotor. For example, by solving this differential equation, one can obtain the velocity function, $$v(t) = v_0 e^{-\frac{kt}{m}},$$

where $v_0$ is the initial velocity—subsequently determined by integrating the velocity over the length of one image frame $\int_0^{\Delta t} v(t)dt = \Delta d$. Since the frame length, Δt is known from the camera settings, and the distance traveled, Δd is also known from image calibration, one can express the initial velocity in terms of known quantities, $$v_0 = \frac{\Delta d}{\frac{m}{k} - \frac{m}{k}e^{-\frac{k\Delta t}{m}}}.$$

For example, using these derived equation along with the quantity values displayed in Table 1, the initial velocity is calculated to be 56.9 m/s. Thus an initial momentum (p=mv) of $2.69 \times 10^{-11}$ Ns and kinetic energy (KE=½mv$^2$) of 0.764 nJ was calculated for a nanomotor with mass of $4.74 \times 10^{-13}$ kg. For example, it is noted that, although it was possible to capture image sequences at frame rates greater than 18,000 fps, the nanomotor velocity was so great that it was not possible in the exemplary implementations to capture more than 2 or 3 frames during motion within the limited field of view. Since this was a memory speed limitation and not a limitation due to amount of light, shutter speeds of at least 1/303,000 seconds were used which could freeze the objects in motion. Thus, the velocity calculations presented herein are an approximation.

Exemplary implementations were performed to demonstrate the ability of the exemplary fuel-functionalized nanomotor to penetrate through dense materials for potential targeted delivery applications. For example, fuel-functionalized nanomotor were propelled into tissue sections from a lamb kidney. FIG. 4A shows a sequence of images 420, 430, and 440 and an illustration 410 of an exemplary fuel-functionalized nanomotor propelled deep and penetrating into a lamb kidney tissue section after using a 44 μsec/1.6 MPa ultrasound pulse. For example, the images 420, 430, and 440 include a dotted yellow circle superimposed on the image to help track the nanomotor's position and a green dotted line superimposed to outline the tissue. Illustration 410 shows an exemplary fuel-functionalized nanomotor 411 penetrating tissue 412 and undergoing propulsion actuated by an ultrasound pulse. Image 420 shows the exemplary fuel-functionalized nanomotor substantially stationary prior to the ultrasound pulse. Image 430 shows the exemplary fuel-functionalized nanomotor impacting the tissue. Image 440 shows the exemplary fuel-functionalized nanomotor 200 μm through the tissue. For example, it is noted that in the image 440, the view of the nanomotor becomes obscured as it penetrates and enters the tissue. The exemplary images 420, 430, and 440 were taken sequentially at a frame rate of 10,000 fps and 10× objective. The exemplary scale bar represents of FIG. 4A 100 μm. A very short ultrasound pulse (e.g., 4.4 μsec) at high pressure (e.g., 3.8 MPa) also provided sufficient thrust for the exemplary fuel-functionalized nanomotor to pierce the kidney tissue, shown in FIG. 10.

Exemplary implementations were conducted by adding diluted PBS solution containing the exemplary ultrasound nanopropulsion devices to 1-2 mm thick tissue sections with a coverslip on top. For example, these thick tissues were used to prevent the exemplary fuel-functionalized nanomotor from going above the tissue and to confirm penetration. For example, simulations using the exemplary fuel-functionalized nanomotor close to the tissue and using extremely short ultrasound pulses (e.g., 10 cycles) consistently demonstrated the ability of the nanomotors to puncture and lodge itself into the kidney, as shown in FIG. 4B. FIG. 4B includes a sequence of images before (image 460), during (image 470) and after (image 480) an exemplary fuel-functionalized nanomotor pierces tissue after a short ultrasound pulse. For example, the images 460, 470, and 480 include a dotted yellow circle superimposed on the image to help track the nanomotor's position. The exemplary images of FIG. 4B were taken sequentially at a frame rate of 10,000 fps. The exemplary scale bar of FIG. 4B represents 40 μm.

FIGS. 5A and 5B show illustrations and images of an exemplary nanomotor device cleaving a diseased tissue section. FIG. 5A shows an exemplary computer-aided graphic illustration 510 portraying a fuel-functionalized nanomotor 511 cleaving apart a diseased kidney tissue section 512 from a healthy tissue section 513, e.g., mimicking a nano surgery operation. The illustration 510 depicts the ability of the ultrasound-triggered fuel-functionalized nanomotors to penetrate, deform, and cleave tissue. For example, the exemplary nanomotors can also be functionalized to target specific cells, such as the diseased tissue 512. The illustration 510 shows the nanomotor 511 capturing and transporting the cleaved diseased tissue section 512a.

FIG. 5B shows sequential images 520, 530, and 540 displaying an exemplary fuel-functionalized nanomotor cleave apart a tissue sample during impact, and capturing and transporting the tissue sample from the section. The image 520 shows the exemplary nanomotor and small tissue sample before a 44 μsec/1.6 MPa ultrasound pulse. The image 530 shows the exemplary nanomotor and its captured small tissue piece while in motion due to the ultrasound pulse. The image 540 shows the exemplary nanomotor and its captured small tissue piece during deceleration. The exemplary images of FIG. 5B were taken sequentially at a frame rate of 10,000 fps (e.g., 0.1 msec intervals) using a 10× objective. For example, the ultrasound pulse pressure can be tuned to actuate the exemplary nanomotors for tissue piercing, deformation, or deep penetration, e.g., depending upon the specifications and tissue degradation restrictions of distinct biomedical applications.

FIG. 6 shows images 610, 620, and 630 that illustrate an exemplary immobilization strategy to a gold-sputtered silicon wafer containing rolled up nanomotors. Image 610 shows the specific binding of fluorescent emulsion particles to the Au-sputtered silicon wafer containing rolled up nanomotors. Image 620 shows the electrostatic binding of the anionic emulsions to the free amine on the Au surface when compared to samples without cysteamine incubation, and panel (c) without emulsion. The exemplary scale bar of FIG. 6 represents 200 μm.

ADV-assisted propulsion is possible for a number of different structures in the nano-millimeter range. The disclosed nanomotors are capable of highly efficient, single-shot, and controllable nanomotor firings, which can be affected by nanomotor fabrication parameters (e.g., size, shape, thickness). For example, exemplary nanomotors having engineered dimensions including, for example, a 40 nm thick rolled nanotube body, 40 μm long nanotube body, and 2.5 μm in diameter, produced ultrafast curvilinear motion when 180 nm diameter-sized PFH emulsions were utilized. Also, the disclosed nanomotors are capable of highly efficient, single-shot, and controllable nanomotor firings, which can be affected by the ultrasound wave trigger settings (e.g., transducer pressure and pulse length).

FIG. 7 shows still frame images 710, 720, and 730 of three exemplary distinct bubble emissions from propelled nanobullets modified with PFH emulsion after different ultrasound pulses. Image 710 shows the bubble emission pattern of streaming bubbles, e.g., which can generally cause spinning nanomotor motion, by utilizing a long pulse (e.g., 444 μsec))/low pressure (e.g., 1.6 MPa) ultrasound pulse. For example, long pulses (e.g., 1000 cycles) produced streams of bubbles and subsequent circular nanomotor motion. Image 720 shows the bubble emission pattern that propels the nanobullets in a substantially linear or semi-linear trajectory by utilizing a medium length pulse (e.g., 44 μsec)/low pressure (e.g., 1.6 MPa) ultrasound pulse. Image 730 shows the diverse bubble formations that are associated with general water cavitation and are not associated with perfluorohexane emulsions by utilizing a relatively medium or long pulse (e.g., ≥44 μsec)/high pressure (e.g., 3.8 MPa)

ultrasound pulse. For example, high transducer pressures (e.g., 3.8 MPa) often caused water cavitation, which when delivered in medium length pulses or large length pulses, resulted in sustained cavitation and solution mixing that created sporadic nanomotor movement. The exemplary images of FIG. 7 included a 1/18000 s frame time.

For example, long nanomotors (e.g., lengths >100 μm) often rotated uncontrollably in circular motion as streams of ADV induced bubbles expelled from both the front and back nanomotor orifices, as shown in FIG. 8. FIG. 8 shows still frame images 810, 820, 830, 840, 850, and 860 displaying bubble emission from both ends of an exemplary large-length (e.g., 100 μm) nanobullet functionalized with PFH emulsion. Image 810 shows a quiescent nanomotor before low pressure/medium pulse length (e.g., 44 μsec, 1.6 MPa) ultrasound pulsing. Image 820 shows bubble formation beginning after the ultrasound pulse, which continues to progress in the subsequent image frames 830, 840, and 850. The dual bubble emission from both ends of the nanomotor induces spinning motion, as shown in the image 860. The exemplary images of FIG. 8 included a 1/18000 s frame time.

Exemplary implementations using thicker nanomotors (e.g., nanomotors with smaller volume interiors), for example, including a 60 μm long nanotube body, a 400 nm thick rolled nanotube body, with a 3 μm in diameter, were shown to explode upon ultrasound triggering, as shown in FIG. 9. FIG. 9 shows still frame images (e.g., 1/18000 s frame time) displaying the breaking or self-destruction of nanomotors modified with PFH emulsion upon ultrasound triggering. Image 910 of FIG. 9 shows the first frame displaying a quiescent nanomotor before a 44 μsec, 1.6 MPa ultrasound pulsing regime. Bubble formation begins within the center of the nanomotor after an ultrasound pulse, as shown in image 920, and the nanomotor begins to rupture, as shown in image 930. The rupture continues to propagate (as shown in images 940-960 until the nanomotor completely breaks into two separate pieces (as shown in panels 970 and 980). The exemplary scale bar of FIG. 9 represents 30 μm.

Exemplary implementations using smaller nanomotors, for example, including a 8 μm long nanotube body with an 800 nm inner diameter, fired less frequently and experienced stochastic locomotion that can be attributed to smaller surface area for emulsion functionalization and less mass for stability, respectively. Additional functionalization tests, revealed that lower boiling point emulsions (e.g., perfluoropentane, with a boiling point of 30° C.) did vaporize more consistently at low pressures but were less stable during functionalization and increased nanomotor explosion during ultrasound triggering.

Figure 10:
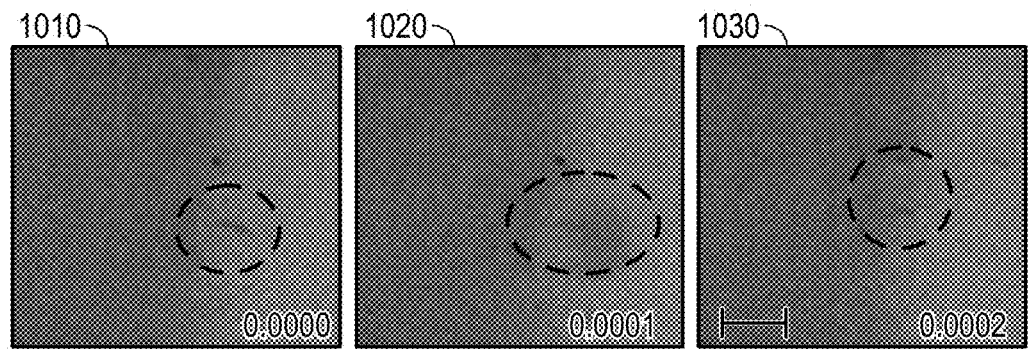
FIG. 10 shows exemplary images that depict the before, during and after effects of an exemplary nanomotor piercing lamb kidney tissue after a short ultrasound pulse.

Exemplary implementations showed that a low pressure/medium pulse length and high pressure/short pulse length ultrasound pulse sequence can produce linear nanomotor locomotion from ADV, e.g., without external water cavitation. FIG. 10 shows a sequence of images that show the before (image 1010), during (image 1020) and after (image 1030) effects of an exemplary nanomotor piercing lamb kidney tissue using a short pulse length/high pressure ultrasound pulse (e.g., 4.4 μsec, 3.8 MPa). The images 1010, 1020, and 1030 include a dotted yellow circle to help track the position of the nanomotor during locomotion. The exemplary images of FIG. 10 were captured sequentially at a frame rate of 10,000 fps. The exemplary scale bar of FIG. 10 represents 60 μm.

Figure 11:
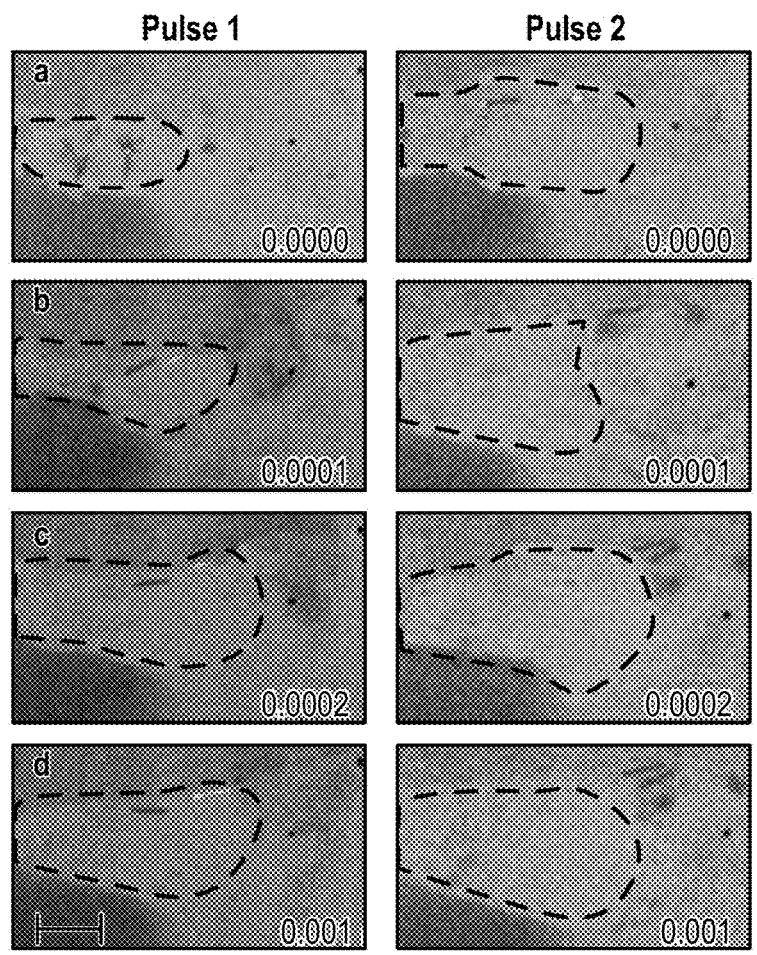
FIG. 11 shows exemplary images depicting the ability of multiple nanomotors to increase the opening of a tissue after ultrasound pulses.

The disclosed technology can include control of multiple nanomotors from the same ultrasound pulse to propel into a tissue section, as shown in FIG. 11. FIG. 11 shows exemplary images of multiple nanomotors propelled through a tissue section which increase the opening of the tissue after two short, high pressure ultrasound pulses (e.g., 4.4 μsec, 3.8 MPa). For example, the exemplary sequential images include yellow accented lines to show the effect of the nanomotors on the tissue opening before (image (a)), during (images (b)-(c)), and after the tissue recoiled (image (d)) for each pulse. The exemplary images of FIG. 11 were taken at a frame rate of 10,000 fps. The exemplary scale bar of FIG. 11 represents 100 μm. For example, the power of multiple ultrasound-triggered nanomotors can be visualized as the nanomotors increase the tissue cavity area by 120% after the first 4.4 μsec/3.8 MPa ultrasound pulse and penetrate the kidney tissue after a second ultrasound pulse.

The disclosed ultrasound-propelled fuel-containing nanomotors offer a safe, low-cost, and effective method to project delivery devices into dense tissue or organs in vivo and in vitro. For example, the described fuel-containing nanomotors possess the ability to accelerate rapidly, acquire significant momentum e.g., $2.69 \times 10^{-11}$ Ns), and reach speeds over 6 m/s, e.g., which are approximately 100 times faster than existing micromachines. The disclosed nanomotor exhibit performance parameters, e.g., speed and force, that enables tissue piercing, deep penetration, deformation, and cleaving capabilities. Furthermore, the nanomotor speed and power can be tailored for diverse applications, e.g., by adjusting the size and shape of the nanomotors and/or the size and composition of the embedded emulsion, as well as the ultrasound pulse parameters. For example, since multiple nanomotors can be simultaneously fired from a single ultrasound pulse, the ultrasound-triggered nanomotor propulsion strategy can have a tremendous impact on diverse biomedical applications, e.g., including, but not limited to, targeted drug delivery, circulating biolistics, gene therapy (e.g., deliver genes directly into cell nuclei for gene therapy), tissue penetration for triggering immune responses, microtissue and artery-cleaning/removal schemes, precision nanosurgery, and cancer therapeutics.

For example, every year about 13,000 patients in the United States die of bladder cancer. Even though bladder cancer can be typically diagnosed in its early superficial stage as a result of microscopic blood in the urine, the disease can have an overall 65% recurrence rate and 30% progression rate, often requiring patients to seek continuous treatment and periodic internal inspections of their bladders. The use of *bacillus* calmette-guerin (BCG) treatment as an intravesical instillation treatment for bladder cancer patients became widely accepted in 1980 when a controlled study showed that the treatment drastically reduced recurrence rates due to the natural inflammatory response triggered by the BCG bacteria burrowing into the cancerous bladder lining. This immunoprophylactic agent has shown a 50-60% effectiveness against small residual tumors and 70% of patients sustain remission for over 5 years. However, the BCG treatment has been shown to cause many side effects and the BCG response is unpredictable. In general, almost all patients (95%) report dysuria, and many experience hematuria (39%), fever (22%) and nausea (22%). Life threatening side effects can occur and can include BCG sepsis, in which the bacteria infection spreads throughout the body via the bloodstream.

In one exemplary application, the disclosed acoustically-propelled nanomotors may be used as an alternative to *Bacillus* Calmette-Guerin (BCG) treatment for bladder cancer. For example, the ultrasound-triggered nanomotors could be introduced and fired into the bladder to create a natural inflammatory response for fighting cancer cells, e.g., similar to the immunoprophylactic effect, to potentially eliminate harmful side effects (e.g., such as sepsis, dysuria, hematuria, nausea, and fever) associated with BCG. Exemplary treatments using the disclosed acoustically-propelled nanomotors may lead to fewer cancer treatments, e.g., as the presence of the disclosed technology maybe sustainable. Additionally, many bacteria related side effects, such as sepsis, may no longer be of concern by using the disclosed technology.

In another aspect of the disclosed technology, receptor-functionalized magnetically-guided ultrasound-powered fuel-free nanowire motors are described towards 'capture and transport' processes in biological media.

The disclosed fuel-free motors possess many capabilities and functionalities, e.g., including magnetic guidance, cargo towing, capture and isolation of biological targets, and operation in untreated biological fluids. For example, template-prepared three-segment Au—Ni—Au nanowire motors can be propelled acoustically by mechanical waves produced by a piezoelectric transducer, e.g., at frequencies around 2.51 MHz. The integrated nickel segment facilitates a magnetically-guided motion as well as for capturing and transporting of large (magnetic) 'cargo' along predetermined trajectories. Efficient locomotion in unprocessed environmental and biological media, such as seawater, serum and saliva, is illustrated. For example, functionalization of the Au segments with bioreceptors can be carried out via self-assembly of a binary alkanethiol monolayer of mercaptoundecanoic acid (MUA) and mercaptohexanol (MCH), followed by EDC/NHS activation and coupling. Such surface modification with bioreceptors, e.g., such as lectin and anti-protein A antibodies bioreceptors, allows the capture and transport of cells and tissue, e.g., such as *E. Coli* and *S. aureus* bacteria (containing protein A at their cell wall), respectively. The unique combination of functions exhibited by the disclosed acoustically-driven, functionalized, fuel-free Au—Ni—Au nanowire motors, e.g., including, but not limited to, fuel-free propulsion, magnetic guidance, molecular recognition, and cargo transport, along with the simple preparation procedures and the minimal deleterious effects of ultrasonic waves make them highly attractive for diverse in vivo biomedical and environmental applications.

The disclosed technology includes the coupling of ultrasound-driven propulsion with magnetic guidance of fuel-free nanowire motors along with their surface functionalization with bioreceptors and cargo towing towards 'capture and transport' of biological targets in relevant matrices. Exemplary implementations using such nanomotors described herein have shown coordinated movement as well as efficient propulsion in relevant biological and environment media. For example, such ultrasound-driven magnetically-guided motors were functionalized with different bioreceptors (e.g., through a mixed MUA/MCH monolayer on their gold segments and EDC-NHS coupling chemistry) to offer selective capture and transport of biological targets.

The disclosed receptor-functionalized magnetically-guided ultrasound-actuated fuel-free nanowire motors can be utilized as an efficient bacterial isolation platform, in which the nanostructures are functionalized with bioreceptors, e.g., such as with lectin and antibody receptors. For example, lectins are readily available glycoproteins that offer an attractive route for recognizing carbohydrate constituents of bacterial surface, via selective binding to cell-wall mono- and oligosaccharide components. For example, ConA, the lectin extracted from *Canavalia ensiformis* used here, is a mannose- and glucose-binding protein able to recognize specific terminal carbohydrates of Gram-negative bacteria such as the *E. coli* surface polysaccharides. On the other hand, antiprotein-A-functionalized nanowires can be used to recognize the protein-A that is innately present in the *Staphylococcus Aureus* (*S. aureus*) cell wall. Lectins and protein-A antibodies have been recently used as the recognition elements of different biosensors for bacterial detection and more recently by catalytic nanomachines-based detection and transport. However, the disclosed receptor-functionalized magnetically-guided ultrasound-actuated fuel-free nanowire motors demonstrate the use of motion-based isolation, which can provide a new and powerful approach for rapid isolation of biological targets and targeted delivery of therapeutic payloads to predetermined destinations.

Figure 12A:
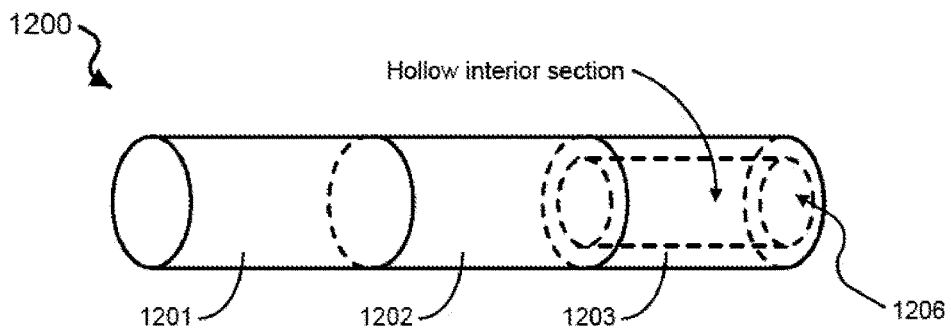
FIGS. 12A and 12B show a schematic of an exemplary ultrasound-propelled magnetically-guided receptor-functionalized nanowire motor device.

FIG. 12A shows a schematic of the nanostructure body of an exemplary ultrasound-propelled magnetically-guided receptor-functionalized fuel-free nanowire motor device 1200. The nanowire motor device 1200 includes a three-segment nanostructure body structured to include an opening 1206 at one end of the nanostructure body and a hollowed interior along the longitudinal direction configured to a particular distance. In other examples, the nanowire motor device 1200 can include two segments, more than three segments, or a single material segment. In the example shown in FIG. 12A, the exemplary three-segment nanostructure body includes a segment 1201 at one end of the body, a segment 1203 at the other end of the nanostructure body, and a segment 1202 in between the segments 1201 and 1203. The nanostructure body of the exemplary nanowire motor device 1200 is configured as a cylindrical, wire-like structure. The nanowire motor device 1200 can also be configured in a conical tube shape, rectangular shape, or a variety of other shapes and geometries of the exterior structure of the nanostructure body. Additionally, the hollow interior section of the nanowire motor device 1200 can be shaped in a cylindrical, conical, hemispheric, faceted or other concave geometry. As shown in the figure, the hollow interior section projects from the opening 1206 through the segment 1203 of the nanostructure body. In other examples, the hollow interior section can project from the opening 1206 through the segments 1203 and 1202 and/or through the segments 1203, 1202, and 1201, as well as through all three exemplary segments of the nanostructure body forming two openings.

In some implementations, the hollow interior section of the nanowire motor device 1200 can include a pitted or rough surface along the interior surface. In other implementations, the hollow interior section of the nanowire motor device 1200 can include smaller particles (e.g., nanoparticles) along the interior surface. In additional implementations, the hollow interior section of the nanowire motor device 1200 can include a layer of a hydrophobic material along the interior surface. The exemplary hydrophobic layer along the interior surface of the nanowire motor device 1200 can, in some implementations, be configured to be rough or pitted and/or include smaller particles (e.g., nanoparticles). These exemplary structures of the interior region of the nanowire motor device 1200 provide cavitation threshold reduction that vaporizes a fluid to produce bubbles that drive the propulsion of the device 1200 in the fluid.

For example, the surface properties and particles on the interior are capable of nucleating acoustic cavitation in water and other liquids through interfacial interactions with the liquid. For example, in water, the energy required to vaporize the water is related to the energy required to break the hydrogen bonds which keep the water in a liquid state. For example, materials to a varying extent can modulate the structure of the water, forcing the molecules to rearrange (creating disorder), partially destabilizing the water "matrix". The consequence of this is that less energy is required to break those hydrogen bonds. In some examples, the disclosed nanowire motor devices are structured to include structural features (e.g., roughness or particles) that produce this effect based on the acoustic energy, such that the roughness on a surface of the device forces water molecules to bend around them and be disordered. In other examples, the disclosed nanowire motor devices are structured to include a hydrophobic surface to force water to minimize its interaction, and thus cause maximal disorder of the water molecules, thereby producing the cavitation effect.

In another example, the disclosed nanowire devices can be structured to include crevices on a hydrophobic surface of the nanostructure body that are configured to be initially dry (e.g., free of liquid), such that, when exposed to liquid, the structured crevices will not fill, thus leaving a gas pocket, providing an efficient nucleation site for acoustic cavitation. Also, for example, if the surface is wet, and bubbles are created in solution for whatever reason, they would have a high probability of sticking in the crevice/would have a high affinity if they happened to encounter it.

Figure 12B:
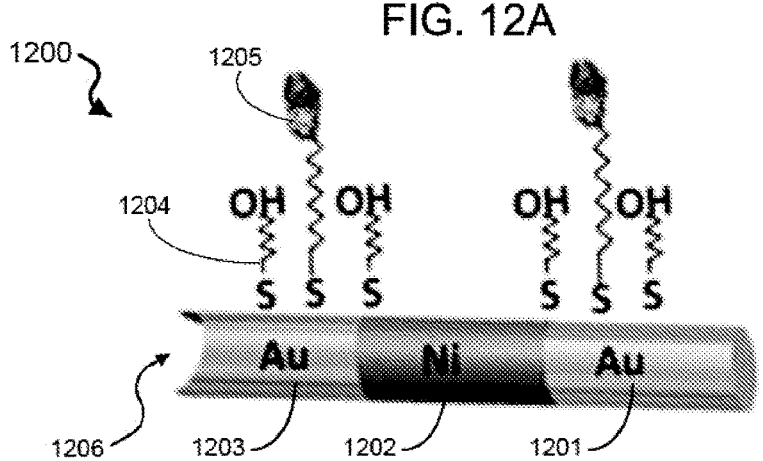

FIG. 12B shows a schematic of the ultrasound-propelled magnetically-guided receptor-functionalized fuel-free nanowire motor device 1200. In the example shown in FIG. 12B, the end segments 1201 and 1203 can be formed of gold, which can facilitate attachment of a linker structure 1204 (e.g., an alkane thiolated linker molecule) that can attach a bioreceptor 1205 at a terminal end of the linker structure 1204 (e.g., by using a terminal functional group, such as an amide or a carboxylate, etc.). In other examples, the segment 1201 and/or the segment 1203 can be formed of another material, e.g., such as platinum, which attaches the bioreceptor 1205 using another attachment scheme. For example, the segment 1202 can be formed of a magnetic material, e.g., such as nickel, that permits external guidance for precision steering of the nanowire motor device 1200. The ultrasound-propelled nanowire motors 1200 can be fabricated through template electrodeposition to form a three-segmented Au/Ni/Au nanowire structure, e.g., including dimensions of 0.2 μm diameter and 3 μm length. In some implementations, the nanowire structure can include a silver sacrificial layer during deposition that allows for the creation of a concave shape in one end of the nanomotor.

Figure 12C:
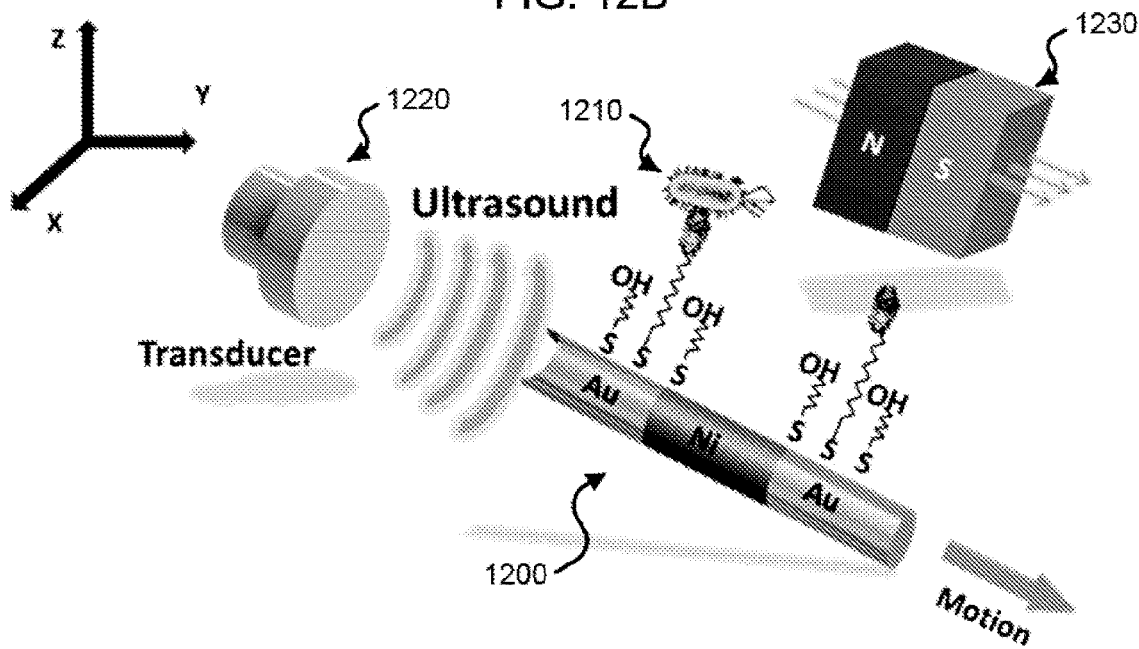
FIG. 12C shows a schematic illustration of an exemplary ultrasound-propelled magnetically-guided receptor-functionalized nanowire motor for selectively capture *E. coli* bacteria.

FIG. 12C shows a schematic illustration of the ultrasound-propelled magnetically-guided receptor-functionalized fuel-free nanowire motor 1200 for selective capture of *E. coli* bacteria 1210. In some examples, the nanowire motor 1200 can be propelled by a pressure gradient formed in a concave or interior region of the nanowire motor 1200 due to ultrasound waves generated by an acoustic energy source (e.g., ultrasound wave transducer) 1220 that penetrate the concave end of the nanowire 1200. In other examples, based on the structure of the interior of the nanowire 1200 having a rough, pitted, and/or hydrophobic interior surface, the nanowire motor 1200 can be propelled by the vaporization of liquid in the fluid forming bubbles due to the reduce the cavitation threshold based on the acoustic waves (e.g., generated by the ultrasound wave transducer 1220). The exemplary nanowire motor 1200 includes nickel in the material of the segment 1202 that allows the nanomotors to be guided using a magnetic field produced by an exemplary magnet 1220 (e.g., such as a 1 T Neodymium magnet). For example, the embedded Ni segment 1202 permits external magnetic alignment, thus allowing the nanomotors to be guided along predetermined trajectories. Modification of the nanomotor's gold surface (e.g., in the segments 1201 and 1203) with an 11-mercatoundecanoic acid (MUA) and 6-mercaptohexanol (MCH) self-assembly monolayer (SAM) allows convenient functionalization of specific bioreceptors 1205 to selectively capture cells or other tissues, e.g., such as *E. coli* or *S. aureus* bacteria in complex media. The exemplary nanowire motors of the disclosed technology include a biocompatible fuel-free nature, which enables their use in many in vitro and in vivo biomedical and environmental applications.

Exemplary magnetically-guided ultrasound-propelled receptor-functionalized fuel-free nanowire motors were utilized in exemplary implementations described in this patent document. Methods of fabrication of these exemplary magnetically-guided ultrasound-propelled nanowire motors are disclosed.

In some examples of the fabrication methods, the following reagents and solutions were used. For example, 6-mercaptohexanol (MCH), 11-mercaptoundecanoic acid (MUA), N-hydroxysuccinimide (NHS), 1-(3-dimethylaminopropyl)-N'-ethylcarbodiimide hydrochloride (EDC), lectin from *Canavalia ensiformes* (Concanavalin A, ConA), acetic acid sodium salt, ethanolamine, 2-(N-morpholino) ethanesulfonic acid (MES), $CaCl_2$ and $MnCl_2$ were obtained from Sigma-Aldrich. The binding buffer (BB) solution included a 0.1 M acetate buffer, pH 5.0, containing 1 mM $Mn^{2+}$ and 1 mM $Ca^{2+}$. These two divalent metals are used to achieve an active ConA conformation for its binding to carbohydrates. A 0.1 M MES buffer solution pH 5.0 was used in the carboxylic activation step. 1 M ethanolamine solution pH 8.5 was used as a blocking agent for amine reactive-esters. Chemicals were analytical-grade reagents and used as received without any further purification and prepared by dilution in 18.2 MΩ cm Milli-Q deionized water when not otherwise specified. Exemplary implementations were carried out at room temperature.

Bacterial strains of *E. coli* NEB 5-α (New England Biolabs) were obtained from the Clinical Microbiology Laboratory, University of California Los Angeles (UCLA), with approval from the UCLA and Veterans Affairs institutional review boards and appropriate Health Insurance Portability and Accountability Act exemptions. The pellets were received in centrifuge tubes and were stored at −80° C. until use. Overnight bacterial cultures were freshly inoculated into Luria broth (LB) and grown to logarithmic phase as measured by the optical density at 600 nm. Concentrations in the logarithmic-phase specimens were determined by serial plating. *S. aureus* cells (e.g., 10% wet w/v of essentially non-viable *S. aureus* Cowan strain cells in 0.04 M sodium phosphate buffer, pH 7.2, 0.15 M NaCl containing 0.05% $NaN_3$) were obtained from Sigma and *S. cerevisiae* were obtained from Science Stuff. Human serum was obtained from Sigma. Saliva samples were collected daily. Drinking water was obtained in a local supermarket. Sea water samples (e.g., pH ~8) were collected from the shores of La Jolla, Calif. All of these samples were inoculated with the appropriate concentration of bacteria at the moment of the exemplary implementation.

Gold nanowire motors used in the exemplary implementations were prepared by a template-directed electrodeposition protocol. For example, a silver film was first sputtered on one side of the porous alumina membrane template containing 200 nm-diameter cylindrical pores (e.g., such as those in Catalogue No. 6809-6022; Whatman, Maidstone, UK) to serve as a working electrode. The membrane was then assembled in a plating cell with an aluminum foil serving as a contact for the sputtered silver. Copper was electrodeposited in the branch area of the membrane from a $CuSO_4.5H_2O$ (1 M) solution, using a charge of 8 C and a potential of −0.95 V (vs. Ag/AgCl reference electrode, along with a Pt-wire counter electrode). Subsequently, gold was plated next from a gold plating solution (Orotemp 24 RTU RACK; Technic Inc.) at −0.95 V (vs. Ag/AgCl), using a charge of 1 C. Nickel was deposited from a nickel plating solution containing $NiCl_2.6H_2O$ (20 g/L), $Ni(H_2NSO_3)_2.4H_2O$ (515 g/L), and $H_3BO_3$ (20 g/L) at −0.95 V (vs. Ag/AgCl) for 1 C. Finally gold was deposited using a charge of 1 C. The sputtered silver layer and copper sacrificial layer were mechanically removed from the membrane by polishing with 3-4 μm alumina slurry, followed by dissolution of any remaining silver with $HNO_3$. The membrane was then dissolved in a NaOH (3 M) solution for 30 min to completely release the nanowires. The nanowires were collected by centrifugation at 6000 rpm for 5 min and were washed repeatedly with Nanopure water (18.2 MΩ cm) until a neutral pH was achieved. The exemplary nanowire solutions were stored in Nanopure water at room temperature.

Implementations using ultrasonic energy were carried out in a cell made in a stainless steel plate 5×5×0.94 mm, covered by four layers of 60 μm Kapton tape with a center hole of 6 mm in diameter as the sample reservoir, and covered by a 18×18×0.15 mm cover slide for reflection of the ultrasound waves and for stability of the solution (e.g., to avoid motion of the solution due to disturbances of the environment). The piezoelectric transducer that produces the ultrasound sine waves (Ferroperm PZ26 disk 10 mm diameter×0.5 mm thickness) was attached to the bottom center of the stainless steel plate. The transducer was fed through a home-made high power totem pole Darlington amplifier by an Agilent 15 MHz arbitrary waveform generator to form an ultrasound waveform, e.g., which can be configured with a controllable voltage amplitude and frequency. For example, in some implementations, a continuous ultrasound sine wave at 2.51 MHz and a varied voltage amplitude from 6 V to 10 V was used, e.g., to increase deflection of the piezoelectric transducer and power of the ultrasonic wave. The electric signal was monitored by a 20 MHz Tektronix 434 storage oscilloscope. The described exemplary implementations were visualized with a Nikon Eclipse 80i illuminated with a Nikon MKII fiber optics light. The images were acquired with a Photometrics CoolSnap HQ2 1392×1040 pixels CCD camera attached to the microscope and were processed with Metamorph 7.7.5 software (Molecular Devices, Sunnyvale, Calif.).

Some of the exemplary nanomotors were functionalized with either lectin protein receptors for the capture and transport of *E. coli* or with anti-protein A antibody for *S. aureus* loading, respectively. The external gold surface of the nanowires were modified by an overnight immersion in a binary mixture of 2.5 mM of MUA and 7.5 mM of MCH thiols in absolute ethanol. After washing with Milli-Q water, carboxylic moieties from the resulting mixed monolayer-modified nanowires were activated with a 20 mM NHS and 10 mM EDC in 0.1 M MES buffer solution pH 5.0 for 30 min and washed with BB solution or PBS solution, respectively, for 1 min. The lectin protein receptors functionalization was achieved by immersing the nanowires in a BB solution containing 9 mg/ml of ConA receptor for 2 h. The antibodies receptors were incubated in 100 μL of anti-Prot-A antibody diluted in PBS (1×) pH 7.2 to a final concentration 750 μg/mL for 2 h. In both cases, the remaining amine reactive-esters from the activated monolayer were blocked with 1 M ethanolamine solution, pH 8.5, for 30 min and later resuspended in BB solution or PBS solution for lectins or antibodies, respectively. Between each incubation and washing steps, the nanomotors were isolated by centrifugation at 6,000 rpm during 4 min. The exemplary implementations were carried out at room temperature. As a control group, unmodified nanowire motors (without any receptor) were prepared using the described protocol (with the SAM assembly, activation and blocking steps), but omitting the addition of the Con A and antibody and carrying out the corresponding incubation in BB solution or PBS solution, respectively.

For exemplary implementations of the disclosed nanomotors that included the detection and isolation of the target bacteria, 2 μL of modified-nanowire suspension were dropped onto a freshly-cleaned glass slide. Once the nanomotors were deemed to possess the proper movement and magnetic guidance, 2 μL of the diluted bacterial cell suspension (prepared in the sample matrix, in the BB or PBS solution) were added to the mixture. Feasibility to capture *E. coli* and *S. aureus* bacteria were tested directly by magnetic guidance of the lectin (or antiprotein A)-modified wires towards the target cells, respectively. Recognition events were monitored by images and videos captured using a Nikon Eclipse 80i upright microscope and a CoolSNAP $HQ^2$ camera, 20× objective and acquired at an exemplary frame rate of 10 frames/s using the Metamorph 7.1 software (Molecular Devices, Sunnyvale, Calif.). The performance of both the lectin-based and antibody-based nanomotors were analyzed in complex matrixes, in which the undiluted sample under study was inoculated with the appropriate concentration of bacteria.

Figure 13:
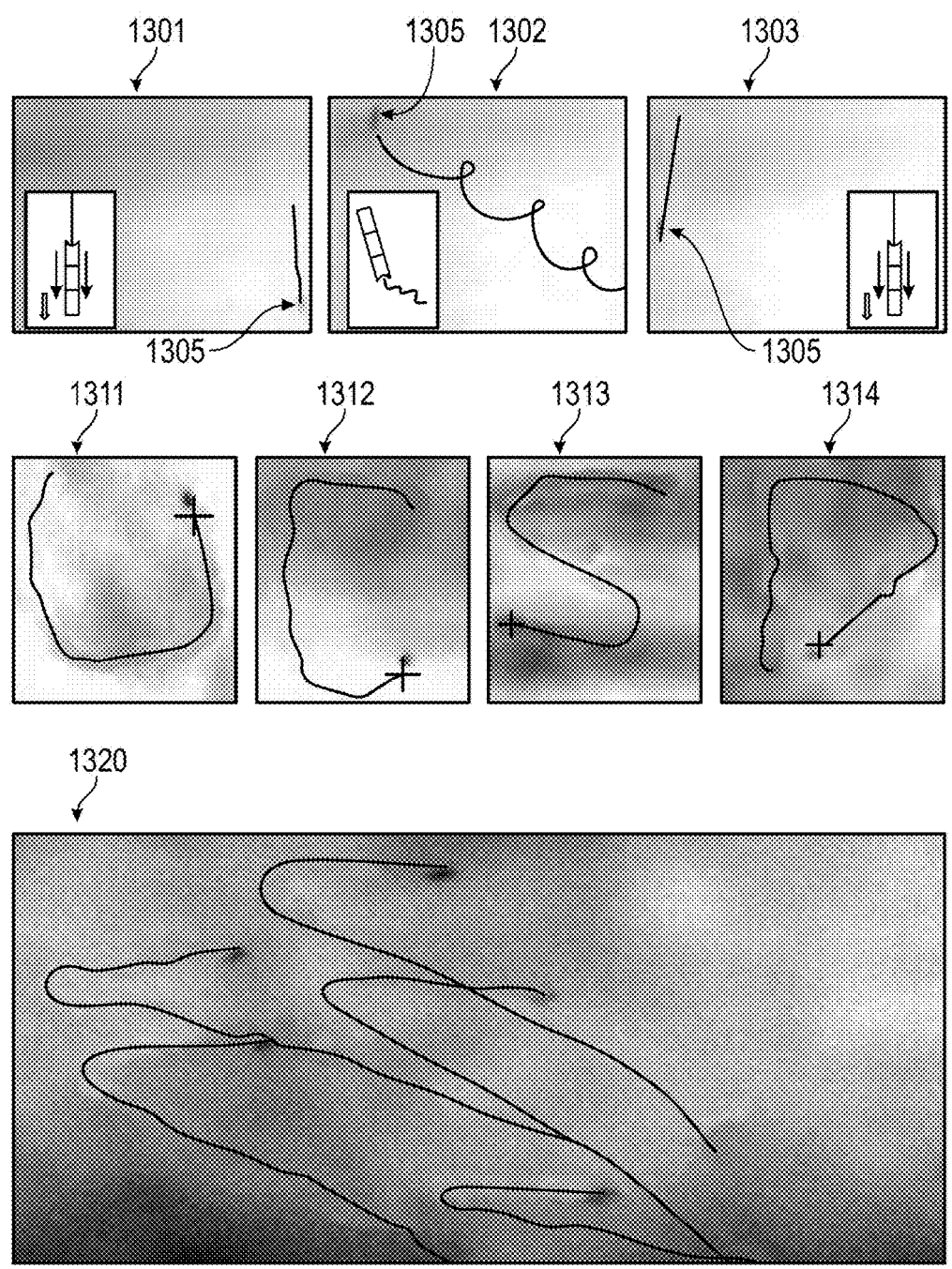
FIG. 13 shows exemplary images demonstrating the magnetic guidance of exemplary ultrasound-propelled nanomotors.

FIG. 13 shows exemplary images demonstrating the magnetic guidance of the exemplary ultrasound-propelled fuel-free nanomotors. FIG. 13 includes a sequence of images 1301, 1302, and 1303 that show the alignment of a nanomotor 1305 with a magnetic field, the random motion of the nanomotor 1305 without a magnetic field, and the redirected alignment of the nanomotor 1305 with magnetic field. The image 1301 shows the magnetically-guided ultrasound propulsion of the nanomotor 1305 having a substantially straight trajectory as the nanomotor 1305 is aligned in the magnetic field. The image 1302 shows the unguided trajectory of the ultrasound-propelled nanomotor 1305 in the absence of a guiding magnetic field. The image 1303 shows the substantially straight trajectory as the nanomotor 1305 is realigned in the magnetic field. FIG. 13 also includes images 1311, 1312, 1313, and 1314 showing the guided trajectories of an exemplary magnetically-steered ultrasound-propelled fuel-free nanomotor along a predetermined route to form the letters U C S D, respectively. FIG. 13 also includes an image 1320 showing the coordinated motion of multiple ultrasound-powered magnetically-guided fuel-free nanomotors of the disclosed technology.

FIG. 13 shows the effect of the magnetic field towards steering the nanowire motors. For example, the nickel segment of the exemplary nanomotor 1305 allows for magnetic alignment. The nanorod is oriented in the direction of the magnetic field produced by a 1 T (Neodymium) magnet. The image 1301 demonstrates how magnetic alignment and straight motion can be produced. When the magnetic field is then turned off, random motion is exhibited, as shown in the image 1302. And when the magnetic field is turned back on, the nanowire motor recovers the alignment and straight motion again, as shown in the image 1303. Guidance over more complex trajectories is also possible by changing the orientation of the applied magnetic field while the nanomotor is propelling. FIG. 13 also shows the 'writing' of the letters UCSD by magnetic guidance of the ultrasound propelled nanomotors, they follow predetermined trajectories at a stable speed, the magnetic field only changes the direction of the nanomotors without interfering with its propulsion, demonstrating the controllability of these devices.

The magnetic guidance can also facilitate the collective coordinated motion of multiple ultrasound-driven fuel-free nanomotors. As shown in the image 1320 of FIG. 13, a group of magnetically guided nanomotors is shown to be regularly distributed, organized, aligned and following a common trajectory at a comparable speed, e.g., behaving like a single entity and demonstrating the reproducibility of these nanomotors. This behavior resembles the swarming of biological species that organize, communicate and act in mass responding to a common stimulus. For example, such coordinated movement of multiple nanomotors can benefit important applications requiring a cooperative action and distributed tasks, e.g., high-yield environmental remediation or highly-sensitive bioisolation and detection.

For example, the movement of these exemplary magnetically-guided ultrasound-driven fuel-free nanomotors may propel from the pressure produced in the concave end of the nanowire by the scattered and reflected ultrasonic waves, which come from different directions. For example, when the main vibration occurs in the direction of the nanorod axis, there is a maximum in the conversion of these waves into axial motion, e.g., maximum speed is achieved. In addition, when the nanowire axis is perpendicular to the principal vibration of the ultrasonic wave there is a minimum, or at times, no propulsion of the fuel-free nanomotor device. Because scattered and reflected waves commonly come from many directions, this last condition is frequently not observed. Special navigation strategies can be considered when these conditions are presented in this kind of devices.

The propulsion of magnetically-steered fuel-free nanowires by ultrasound is schematically illustrated in FIGS. 14A-14B. The schematic illustration of FIG. 14A shows the alignment conditions of a nanowire motor 1400 with vibration energy 1410 of ultrasound waves to achieve maximum speed, in which the axis of nanowire is aligned in direction of the ultrasound wave. FIG. 14B shows an example of reduced speed of the nanowire motor 1400 when outside the axis. For example, as shown in FIGS. 14A and 14B, the vibration energy 1410 is emanating from the top of the schematic illustration. In FIG. 14A, the nanowire motor 1400 is aligned with the vibration energy 1410 along the axis through the nanowire structure, e.g., including the hollow interior section, which can result in a maximum moment transfer and highest speed achieved. In FIG. 14B, the nanowire motor 1400 has been steered out of the axis of the ultrasound waves, e.g., by an applied magnetic field acted on the nanowire motor 1400, which can cause a reduction of moment transfer and consequently a reduction in speed. FIG. 14C shows an image 1420 showing the trajectory of an exemplary ultrasound-propelled magnetically-guided fuel-free nanowire motor 1421 changing directions. The size of the arrows shown in the image 1420 is related to the speed magnitude of the nanowire motor 1421.

Figure 15A:
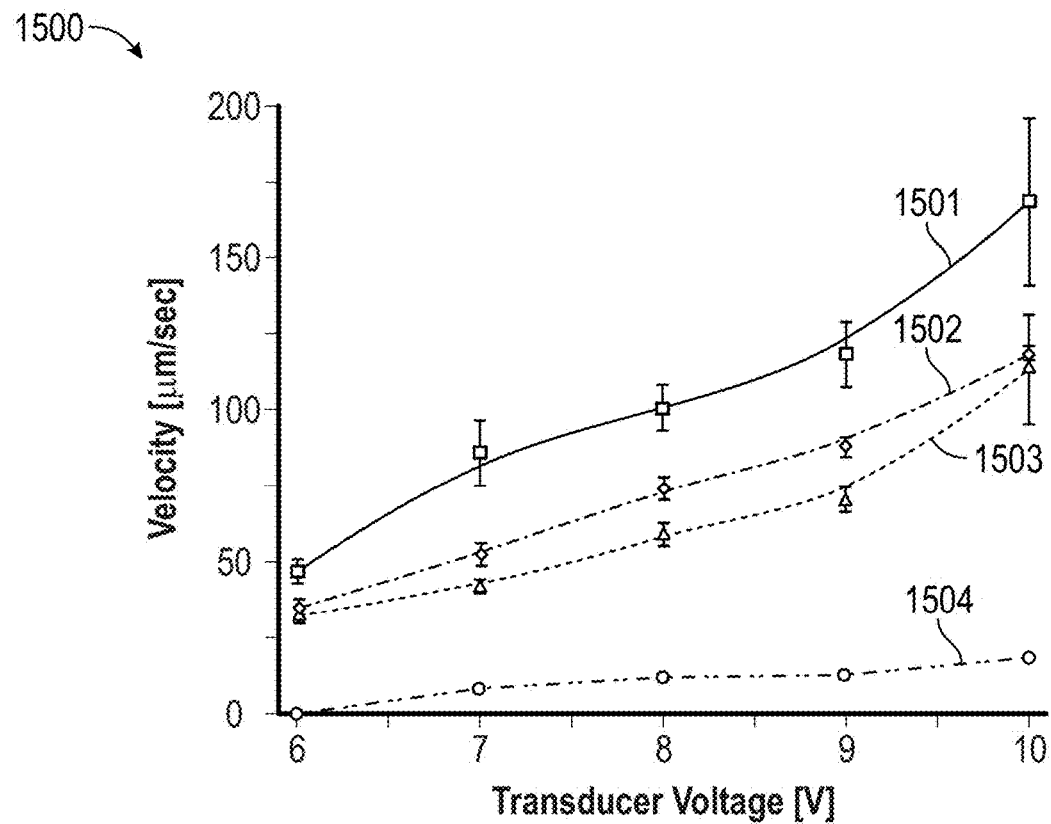
FIGS. 15A and 15B show a data plot and image, respectively, demonstrating the speed dependence of nanomotors upon the ultrasound transducer voltage (power) in different media.
Figure 15B:
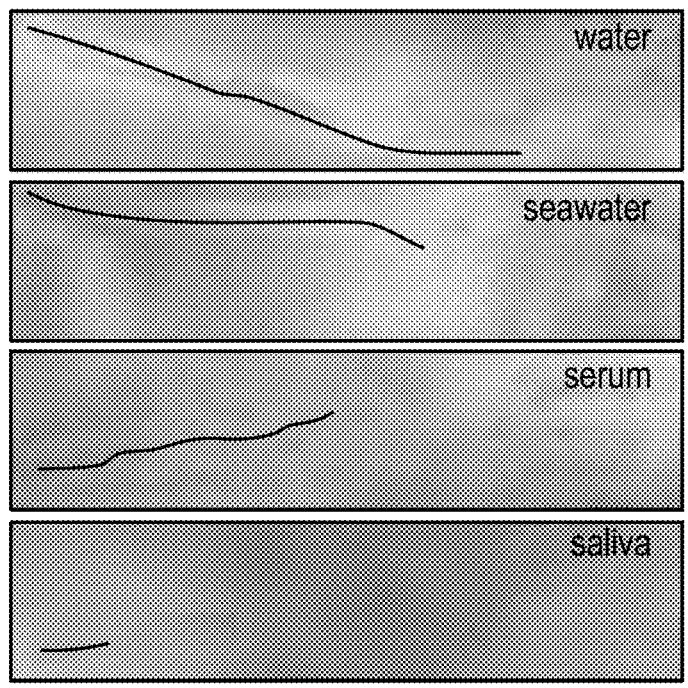

FIGS. 15A and 15B show a data plot 1500 and an image 1550, respectively, demonstrating the relationship of the speed of the ultrasound-propelled fuel-free nanomotors upon the ultrasound transducer voltage (power) in different media. For example, measurements were taken at 2.51 MHz, and the exemplary tri-segment Au/Ni/Au nanowires were fabricated to be 3 μm. As shown in the plot 1500, speed varies with viscosity of the fluid. The data 1501 shows the velocity in water (e.g., 101 μm/s). The data 1502 shows the velocity in seawater (e.g., 80 μm/s). The data 1503 shows the velocity in serum (e.g., 57 μm/s). The data 1504 shows the velocity in saliva (e.g., 14 μm/s).

For example, many existing nanomotor designs include restrictions in their ability to operate in media with high ionic strength and biofluidics. The disclosed nanomotors are shown in FIG. 15 to operate in high ionic strength media, e.g., such as seawater, in addition to serum and saliva as examples for biological fluidics.

The speed of the exemplary ultrasound-propelled magnetically-guided receptor-functionalized fuel-free nanowire motor devices can be tuned and controlled. In some implementations, the speed can be tuned and controlled by tailoring the voltage amplitude applied to the piezoelectric transducer. For example, as the deflection of the transducer can depend on the voltage, the intensity of the ultrasound wave can be directly related to this parameter and hence to the nanomotor speed.

In addition, the viscosity of the fluid medium can affect the speed of the nanomotors. As shown in the data plot 1500 of FIG. 15A, the linear speed response to the applied voltage was shown to be fastest speed in water, e.g., ranging from 50 to 170 μm s$^{-1}$ at applied voltages from 6 to 10 Volts correspondingly, followed by seawater (e.g., 40 to 120 μm s$^{-1}$), serum (e.g., 35 to 110 μm s$^{-1}$) and the slowest speed in saliva (e.g., 0 to 20 μm s$^{-1}$). For example, due to the mechanical nature of ultrasound waves, this reduction in speed is attributed mainly to the viscosity of the fluid, and no other electrical or chemical agents. These features make the ultrasound-propelled nanomotors very attractive for navigation purposes, because they can be accelerated on demand by varying the applied voltage, instead of the impractical modification of fuel concentration as in fuel-based nanomotors. In addition, for example, the broad types of media in which the disclosed nanomotors can be ultrasonically propelled provides an attractive feature, as well as the environmentally friendly nature of the ultrasound waves.

The described ultrasound-propelled magnetically-guided receptor-functionalized fuel-free nanowire motor devices can be implemented in bioisolation applications to capture and transport cells and tissues, e.g., without reliance on an external fuel supply or limitations on the fluid environment.

FIGS. 16A-16C show a series of images demonstrating the ability of the disclosed ultrasound-propelled magnetically-guided receptor-functionalized fuel-free nanowire motor devices to capture and transport a load. FIG. 16A shows the approach, capture, and transport of an exemplary 0.89 μm magnetic bead by an exemplary Au/Ni/Au unmodified ultrasound-propelled nanomotor. FIG. 16B shows the approach, capture, and transport of an exemplary *E. coli* bacteria cell by an exemplary lectin-modified Au/Ni/Au ultrasound-propelled nanomotor. FIG. 16C shows the approach, contact, and non-capture of an *E. coli* bacteria cell by an exemplary unmodified Au/Ni/Au ultrasound-propelled nanomotor.

The magnetic properties of the Ni segment allow the exemplary acoustically-driven Au—Ni—Au nanowires to be utilized for not only magnetic guidance, but also for the pick-up and transport of magnetic microparticles along predetermined paths. As illustrated in FIG. 16A, an ultrasound-powered nanomotor can be guided by the external magnetic field to approach a preselected magnetic microsphere, e.g., which was implemented at a speed of 35.6 μm s$^{-1}$. A dynamic loading of the microsphere onto the nanomotor was observed when they come within reach of significant magnetic force. Subsequently, for example, the nanomotor transported the microsphere with ~57% of its original speed (e.g., 20.3 μm s$^{-1}$) along a predetermined path.

The nanowire functionalization protocol can be implemented for efficient Con A lectin-bacteria interaction and locomotion. As illustrated in FIG. 12B, functionalization can be accomplished by conjugating an exemplary lectin bioreceptor 1205 to the two gold segments 1201 and 1203 of the nanowire motor 1200 using a linker structure 1204, e.g., such as an alkanethiol SAM. For example, in an exemplary implementation of the described ultrasound-propelled magnetically-guided receptor-functionalized fuel-free nanowire motor devices, a mixture of MUA MCH was used to create the binary SAM while 1-ethyl-3-(3-dimethylaminopropyl) carbodiimide (EDC)/N-hydroxysuccinimide (NHS) chemistry was used to activate the MUA carboxyl terminated groups for conjugation with ConA. For example, to promote favorable target accessibility while minimizing non-specific adsorption, the binary SAM was prepared using 2.5 mM MUA and 7.5 mM MCH as optimal alkanethiol concentrations. For example, such surface modification of the Au/Ni/Au nanowires did not affect their speed, thus holding the original exemplary average speed of $-50$ µm s$^{-1}$ at 7 V, and towing force of 0.42 pN, enough to transport 2 µm cells at 10 body length per second. After the SAM activation, the lectin receptor was immobilized via EDC/NHS coupling using a binding buffer (BB) solution containing 9 mg/mL of ConA. This process did not appreciably affect the nanoengine speed. In contrast, for example, an appreciable reduction in locomotion speed and therefore towing capabilities of catalytically propelled nanomotors have been reported after both SAM formation and bioreceptor functionalization processes. Overall, the high speed of the modified nanoengines, their high towing capacity and the strong lectin/bacteria interaction, ensure efficient bacteria pick-up and transport.

FIG. 16B shows the interaction between the ConA-functionalized nanowires and the *E. coli* target bacteria in an ultrasound-supplied aqueous environment. For example, concavalin A interacts with the O-antigen of the *E. coli* cell wall. Utilizing the nanowire magnetic properties, the exemplary functionalized nanowire can be guided to approach at 43.7 µm s$^{-1}$ rapidly capturing any of the *E. coli* bacteria around it and then transporting the cargo through a preselected trajectory, although the nanomotor speed may be decreased to 24.7 µm s$^{-1}$, around 56% of the exemplary original speed.

For example, to calculate its dragging force FD, Stokes Equation (6) can be used for a cylinder, e.g., with L=3 µm and r=0.1 µm being the length and radius of the nanomotors, respectively, µ the viscosity of the fluid and v the nanomotor speed, resulting in a towing force of 0.284 pN.

$$F_D = \frac{2\pi\mu L v}{\ln\frac{L}{r} - 0.5} \quad (6)$$

In this exemplary case, the *E. coli* bacterium (e.g., 1-2 µm) is about the same size of the nanowire. Assuming that the bacteria is a sphere of radius 0.7 µm, it is possible to use the Stokes Equation (7) for a cell, to calculate the dragging force necessary to transport it at 2 body lengths per second, resulting in a dragging force of 0.037 pN.

$$F_{Dcell} = 6\pi\mu r v \quad (7)$$

The transport of large cargo demonstrated the strong towing force of these ultrasound-propelled nanowires. In addition, it is possible to increase this towing force on demand up to 1.1 pN by increasing the power of the ultrasound waves and hence its speed.

A control group of non-modified nanomotors were also used to interact with *E. coli*, after several trials of interaction with the bacteria >30, no attachment was achieved. The results as shown in FIG. 16C reflect no unspecific interaction between non-modified nanomotors and *E. coli*, demonstrating the high selectivity of the nanodevices.

Exemplary implementations were implemented to extend the application of the ultrasound-powered fuel-free nanowire motors towards different bioanalytes. For example, nanowires were functionalized with a protein A antibody and tested the feasibility to pick up and transport *Staphylococcus Aureus* (*S. Aureus*) bacteria. For example, functionalization was achieved by using the same EDC/NHS coupling chemistry through SAMs of thiols in an analogous manner as used for ConA lectins functionalization, as explained before. Additionally, the exemplary functionalized ultrasound-powered fuel-free nanowire motors were compared with functionalized catalytic tubular microengines. Conditions to functionalize the catalytic tubular microengines were optimized for the efficient protein-antibody interaction and locomotion. The results of the exemplary comparative implementations showed that, unlike catalytic-propelled engines, in which functionalization with protein A antibodies speed down their motion, navigation speed of the exemplary functionalized ultrasound-powered fuel-free nanowire motors didn't substantially change after functionalization with the antibodies. Results of the exemplary implementations showed the capture of two *S. Aureus* bacteria containing protein A on their cellular walls, the nanomotors have initial speeds of 45 µm s$^{-1}$ corresponding to 0.3 pN dragging force according to Stokes Equation (6). For example, after the pick-up, it transported the 2 µm bacteria at a reduced speed of 10 µm s$^{-1}$, demonstrating rapid isolation and transport of multiple cargos. Thus, the fuel-free propulsion, magnetic guidance, functionalization options and strong towing force provide a large palette of detection and separation applications for the disclosed ultrasound-propelled nanomotors.

Described are acoustically-driven nanomotors with enhanced capabilities, performance and functionalities, e.g., including magnetic guidance, cargo towing, sorting of biological targets, and operation in diverse media. The disclosed fuel-free driven nanomotor propelled by ultrasonic waves can be applied in an environmentally- and biomedically-friendly manner for pick-up and transport of varied cargo in different media. For example, implementations of the exemplary tri-segmented 3 µm sized Au/Ni/Au nanomotors including a magnetic Ni segment and modification of the gold surface with functionalized alkanethiol monolayers was shown. For example, their exemplary hollowed tail ends enabled an exceptional driving mechanism using penetrating ultrasound waves that induced a pressure gradient inside. Furthermore for example, the ultrasound energy can be applied at low therapeutic levels, and magnetically guided motion can be utilized. For example, eliminating the use of high concentrations of hydrogen peroxide as a fuel for the movement and propulsion of nanowires and nanomotors, biomedical applications can be more feasible, e.g., reducing the use of any excess toxic wastes for the body as well as the environment. For example, in an in vitro application, the exemplary magnetic guidance can allow directed motion of acoustically-driven motors along preselected paths of complex microchip channel networks. The disclosed ultrasound-driven nanowire motors can be prepared in large scale using a simple template electrodeposition protocol and offer considerable promise for diverse practical applications. With enhanced performance, new capabilities, and functionalities, the described ultrasound-powered nanomotors are expected to perform complex and diverse operations and benefit different areas of biomedical and environmental interest.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Only a few implementations and examples are described and other implementations, enhancements and variations can be made based on what is described and illustrated in this patent document.

What is claimed is:

1. An ultrasound responsive propulsion system, comprising:
    an ultrasound transducer that generates an ultrasound wave;
    a tube that includes one or more layers including an inner layer inside the tube having an electrostatic surface; and
    an ultrasound-responsive substance coupled to the inner layer and configured to form gaseous bubbles in a fluid in response to the ultrasound wave, wherein the bubbles exit the tube to propel the tube to move in the fluid.

2. The ultrasound responsive propulsion system of claim 1, wherein the tube is structured to include a first large opening and a second small opening that are on opposite ends of the tube, and a tube body connecting the first large opening and the second small opening and having a cross section spatially reducing in size along a longitudinal direction from the first large opening to the second small opening.

3. The ultrasound responsive propulsion system of claim 2, wherein the bubbles exit the tube from the first large opening to propel the tube to move in the fluid.

4. The ultrasound responsive propulsion system of claim 1, wherein the one or more layers include at least one of a titanium layer, a nickel layer, or a gold layer; or wherein the one or more layers include a gold layer and a polyaniline layer.

5. The ultrasound responsive propulsion system of claim 1, wherein the ultrasound-responsive substance include a nano sized liquid emulsion.

6. The ultrasound responsive propulsion system of claim 5, wherein the liquid emulsion includes perfluorocarbon.

7. The ultrasound responsive propulsion system of claim 1, wherein the inner layer is functionalized with a positively charged monolayer to form the electrostatic surface.

8. The ultrasound responsive propulsion system of claim 7, wherein the ultrasound-responsive substance is stabilized to the electrostatic surface by an anionic surfactant.

9. The ultrasound responsive propulsion system of claim 1, wherein the tube has a diameter in a range of between one nanometer and one millimeter; or wherein the tube has a length between 1 micrometer and 100 micrometers.

10. The ultrasound responsive propulsion system of claim 1, wherein the fluid is a biological fluid~ and the device is capable to propel through the biological fluid including biological tissue, wherein the device is capable to penetrate, puncture, and cleave the biological tissue.

11. The ultrasound responsive propulsion system of claim 1, further comprising a payload substance coupled to the tube, wherein the payload substance includes at least one of a drug, an imaging agent, an enzyme, a nucleic acid, a protein, immunostimulatory compound, a viral vector, or a biomolecule.

12. The ultrasound responsive propulsion system of claim 1, wherein the one or more layers of the tube further include a steering structure that interacts with an external control to steer a pointing direction of the tube while being propelled by the bubbles.

13. The ultrasound responsive propulsion system of claim 12, wherein the steering structure includes a magnetic material that interacts with an external magnetic field to magnetically steer the pointing direction of the tube.

14. The ultrasound responsive propulsion system of claim 1, further comprising a ligand molecule coupled to the tube, the ligand molecule having an affinity to a targeted molecule, wherein the ligand molecule includes at least one of an antibody, single-stranded oligonucleotide, aptamer, lectin, or peptide.

15. The ultrasound responsive propulsion system of claim 14, wherein the ligand molecule includes the antibody and the targeted molecule includes an antigen having a binding affinity to the antibody, the antigen located on a cell that attaches to the tube at the ligand molecule; or
    wherein the ligand molecule includes the single-stranded oligonucleotide, the single-stranded oligonucleotide having an affinity to a complimentary binding site of a target nucleic acid; or
    wherein the ligand molecule includes the aptamer, the aptamer having an affinity to a protein-based molecule; or
    wherein the ligand molecule includes the lectin, the lectin having an affinity to a receptor site of a bacteria cell.

16. A method of using a tubular structure to collect a target substance in a fluid, comprising:
    supplying a tube in a fluid medium, the tube including an ultrasound-responsive substance on an inner wall of the tube to generate gaseous bubbles in response to ultrasonic acoustic energy;
    applying an ultrasound pulse to cause vaporization of the ultrasound-responsive substance to form the gaseous bubbles and to propel the tube in the fluid medium; and
    using a molecular layer on an external surface of the tube to selectively collect a target substance in the fluid while the tube is propelled in the fluid.

17. The method of claim 16, wherein the molecular layer includes a self-assembled monolayer coupled to the external surface and a ligand molecule coupled to an outer end of the self-assembled monolayer, the ligand molecule having an affinity to the target substance.

18. The method of claim 17, wherein the ligand molecule is at least one of an antibody, single-stranded oligonucleotide, aptamer, lectin, or peptide, and wherein the target substance includes at least one of cancer cells, bacterial cells, nucleic acids or protein antigens.

19. The method of claim 16, further comprising:
guiding the tube with an external control to steer a pointing direction of the tube while being propelled by the bubbles.

20. The method of claim 19, wherein the external control includes an external magnetic field to magnetically steer the pointing direction of the tube.

21. The method of claim 16, wherein the fluid medium is a biological fluid and the tube propels through the biological fluid including biological tissue.

22. The method of claim 21, wherein the tube penetrates, punctures, and cleaves the biological tissue.

23. The method of claim 16, wherein the tube further comprises a payload substance attached to the molecular layer of the tube, wherein the payload substance includes at least one of a drug, an imaging agent, an enzyme, a nucleic acid, a protein, immunostimulatory compound, a viral vector, or a biomolecule.

24. A device to locomote in a fluid by acoustic energy, comprising:
an ultrasound transducer to produce an external ultrasound pulse;
two or more segments structured to form a rod having an interior cavity spanning from an opening at one end of the rod,
wherein at least one of the segments includes an outer surface of a modifiable material capable of being functionalized,
wherein the rod is structured to interact with the external ultrasound pulse to create a pressure gradient within the interior cavity to propel the device in the fluid.

25. The device of claim 24, wherein the interior cavity forms one of a cylindrical, conical, hemispheric, or faceted shape from the opening at the one end of the rod.

26. The device of claim 24, wherein the rod includes a magnetic material to interact with an external magnetic field in facilitating propulsion of the device.

27. The device of claim 24, wherein the rod is structured to include a second opening at the opposite end of the rod having a smaller diameter than the opening, the opening and the second opening connected by the internal cavity.

28. The device of claim 24, wherein the two or more segments include at least one gold segment and a magnetic segment.

29. The device of claim 24, wherein the rod has a diameter in a range of between one nanometer and one millimeter; or wherein the rod has a length between 1 micrometer and 100 micrometer.

30. The device of claim 24, wherein the fluid is a biological fluid, the device is capable to propel through in the biological fluid including biological tissue, wherein the device is capable to penetrate, puncture, and cleave the biological tissue.

31. The device of claim 24, wherein at least one of the segments includes a steering structure that interacts with an external control to steer a pointing direction of the rod during propulsion.

32. The device of claim 31, wherein the steering structure includes a magnetic material that interacts with an external magnetic field to magnetically steer the pointing direction of the rod.

33. The device of claim 24, further comprising:
a molecular layer formed on the modifiable material and including a ligand molecule, the molecular layer structured to attach a target substance having a receptor site with a binding affinity to the ligand molecule.

34. The device of claim 33, wherein the ligand molecule is an antibody and the targeted molecule includes an antigen having a binding affinity to the antibody, the antigen located on a cell that attaches to the rod at the ligand molecule; or
wherein the ligand molecule is a single-stranded oligonucleotide having an affinity to a complimentary binding site of a target nucleic acid; or
wherein the ligand molecule is an aptamer having an affinity to a protein-based molecule; or
wherein the ligand molecule is a lectin having an affinity to a receptor site of a bacteria cell.

35. The device of claim 24, further comprising a payload substance coupled to the molecular layer, wherein the payload substance includes at least one of a drug, an imaging agent, an enzyme, a nucleic acid, a protein, immunostimulatory compound, a viral vector, or a biomolecule.

36. A method of using a nanowire motor to collect a target substance in a fluid, comprising:
supplying a rod in a fluid medium, the rod formed of two or more segments and including an interior cavity spanning from an opening at one end of the rod;
applying an ultrasound pulse to create a pressure gradient within the internal cavity to propel the rod in the fluid medium; and
using a molecular layer on an external surface of the rod to selectively collect a target substance in the fluid medium.

37. The method of claim 36, wherein the molecular layer includes a self-assembled monolayer coupled to the external surface and a ligand molecule coupled to an outer end of the self-assembled monolayer, the ligand molecule having an affinity to the target substance.

38. The method of claim 37, wherein the ligand molecule is at least one of an antibody, single-stranded oligonucleotide, aptamer, lectin, or peptide, and wherein the target substance includes at least one of cancer cells, bacterial cells, nucleic acids or protein antigens.

39. The method of claim 36, further comprising:
guiding the rod with an external control to steer a pointing direction of the rod during propulsion.

40. The method of claim 39, wherein the external control includes an external magnetic field to magnetically steer the pointing direction of the rod.

41. The method of claim 36, wherein the fluid medium is a biological fluid and the rod propels through in the biological fluid including biological tissue.

42. The method of claim 41, wherein the rod penetrates, punctures, and cleaves the biological tissue.

43. The method of claim 36, wherein the rod further comprises a payload substance attached to the molecular layer of the rod, wherein the payload substance includes at least one of a drug, an imaging agent, an enzyme, a nucleic acid, a protein, immunostimulatory compound, a viral vector, or a biomolecule.

* * * * *

UNITED STATES PATENT AND TRADEMARK OFFICE
CERTIFICATE OF CORRECTION

PATENT NO. : 9,726,114 B2
APPLICATION NO. : 14/379279
DATED : August 8, 2017
INVENTOR(S) : Joseph Wang et al.

Page 1 of 1

It is certified that error appears in the above-identified patent and that said Letters Patent is hereby corrected as shown below:

In the Specification

STATEMENT REGARDING FEDERALLY SPONSORED RESEARCH OR DEVELOPMENT section, Column 1, Lines 20-24, delete:
"This invention was made with government support under grant CA119335 and CA153915 awarded by the National Institutes of Health (NIH), along with grant CBET 0853375, awarded by the National Science Foundation (NSF). The government has certain rights in the invention."

And insert:
--This invention was made with government support under CA119335 and CA153915 awarded by the National Institutes of Health, and under CBET0853375 awarded by the National Science Foundation, and under HDTRA1-13-1-0002 awarded by the Defense Threat Reduction Agency, Department of Defense. The government has certain rights in the invention.--

Signed and Sealed this
Sixteenth Day of December, 2025

John A. Squires
*Director of the United States Patent and Trademark Office*